(12) United States Patent
Polvino

(10) Patent No.: US 8,039,457 B2
(45) Date of Patent: Oct. 18, 2011

(54) METHOD OF STIMULATING THE MOTILITY OF THE GASTROINTESTINAL SYSTEM USING GROWTH HORMONE SECRETAGOGUES

(75) Inventor: William J. Polvino, Tinton Falls, NJ (US)

(73) Assignee: Helsinn Therapeutics (U.S.), Inc., Bridgewater, NJ (US)

( * ) Notice: Subject to any disclaimer, the term of this patent is extended or adjusted under 35 U.S.C. 154(b) by 0 days.

(21) Appl. No.: 12/631,490

(22) Filed: Dec. 4, 2009

(65) Prior Publication Data

US 2010/0087381 A1 Apr. 8, 2010

Related U.S. Application Data

(63) Continuation of application No. 11/203,639, filed on Aug. 12, 2005, now abandoned.

(60) Provisional application No. 60/600,959, filed on Aug. 12, 2004.

(51) Int. Cl.
*A61K 31/33* (2006.01)
(52) U.S. Cl. ...................................... 514/183
(58) Field of Classification Search .................. 514/183
See application file for complete search history.

(56) References Cited

U.S. PATENT DOCUMENTS

| | | | |
|---|---|---|---|
| 5,767,085 A | 6/1998 | Johansen et al. | |
| 5,977,178 A | 11/1999 | Hansen et al. | |
| 6,083,908 A | 7/2000 | Ankersen et al. | |
| 6,127,354 A | 10/2000 | Peschke et al. | |
| 6,127,391 A | 10/2000 | Hansen et al. | |
| 6,274,584 B1 | 8/2001 | Peschke et al. | |
| 6,286,927 B1 | 9/2001 | Taneya et al. | |
| 6,303,620 B1 | 10/2001 | Hansen et al. | |
| 6,451,806 B2 | 9/2002 | Farrar | |
| 6,469,030 B2 * | 10/2002 | Farrar et al. | 514/331 |
| 6,494,563 B2 | 12/2002 | Taneya et al. | |
| 6,548,501 B2 | 4/2003 | Hakkinen | |
| 6,555,570 B2 | 4/2003 | Hansen et al. | |
| 6,566,337 B1 | 5/2003 | Ankersen et al. | |
| 6,576,648 B2 | 6/2003 | Ankersen et al. | |
| 6,919,315 B1 | 7/2005 | Peschke et al. | |
| 6,939,880 B2 | 9/2005 | Hansen et al. | |
| 2002/0042419 A1 | 4/2002 | Hakkinen | |
| 2005/0277677 A1 | 12/2005 | Heiman et al. | |
| 2007/0021331 A1 | 1/2007 | Fraser | |
| 2007/0191283 A1 | 8/2007 | Polvino | |

FOREIGN PATENT DOCUMENTS

| | | |
|---|---|---|
| WO | WO 00/001726 | 1/2000 |
| WO | WO 01/34593 | 5/2001 |

OTHER PUBLICATIONS

Han, J. 'Advances in the Characterization of Pharmaceutical Hydrates' Trends in Bio/Pharmaceutical Industry, vol. 3, p. 25-29, 2006.*
International Preliminary Report Patentability dated Feb. 6, 2007 in PCTUS05028851.
Written Opinion and International Search Report dated Aug. 21, 2006 in PCTUS05028851.
International Search Report dated Feb. 21, 2009 in PCTUS08/13156.
Vippagunta et al. "Crystalline Solids" Advanced Drug Del Rev, vol. 48, p. 3-26, 2001.
Supplementary European Search Report dated Jul. 22, 2010 in EP Application 08742733.2.2123 (PCT/US08/004640).
Liu, Y-L et al., "Ghrelin alleviates cancer chemotherapy-associated dyspepsia in rodents," Cancer Chemotherapy and Pharmacology, vol. 58, No. 3, pp. 326-333, Sep. 2006.
Rudd, John A. et al., "Anti-emetic activity of ghrelin in ferrets exposed to the cytotoxic anti-cancer agent cisplatin," Neuroscience Letters, vol. 392, No. 1-2, pp. 79-83, Jan. 9, 2006.
Paul, Bernhard J. et al., "A Practical Synthesis of the Pseudotripeptide RC-1291," Organic Process Research & Development, vol. 10, No. 2, pp. 339-345, 2006.
Yang, L., et al., "1-[2-(R)-(2-amino-2-methylpropionylamino)-3-(1H-indol-3-yl)propionyl]-3-benzylpiperidine-3(S)-carboxylic acid ethyl ester (L-163,540): a potent, orally bioavailable, and short-duration growth hormone secretagogue," Journal of Medicinal Chemistry, vol. 41, No. 14, pp. 2439-2441, Jul. 2, 1998.

* cited by examiner

*Primary Examiner* — Brandon Fetterolf
*Assistant Examiner* — Christopher R Stone
(74) *Attorney, Agent, or Firm* — Clark G. Sullivan; Arnall Golden Gregory LLP

(57) ABSTRACT

The present invention relates to a method of stimulating the motility of the gastrointestinal system in a subject in need thereof, wherein the subject suffers from maladies (i.e., disorders or diseases) of the gastrointestinal system. The method comprises administering to a subject in need thereof a therapeutically effective amount of a growth hormone secretagogue compound or a pharmaceutically acceptable salt, hydrate or solvate thereof. The growth hormone secretagogue can be co-administered with a laxative, a $H_2$ receptor antagonist, a serotonin 5-$HT_4$ agonist, an antacid, an opioid antagonist, a proton pump inhibitor, a motilin receptor agonist, dopamine antagonist, a cholinergic agonist, a cholinesterase inhibitor, somatostatin, octreotide, or any combination thereof.

16 Claims, 7 Drawing Sheets

METHOD OF STIMULATING THE MOTILITY OF THE GASTROINTESTINAL SYSTEM USING GROWTH HORMONE SECRETAGOGUES

This application claims priority to U.S. Provisional Patent Application Ser. No. 60/600,959 filed Aug. 12, 2004, the disclosure of which is incorporated herein by reference in its entirety.

BACKGROUND OF THE INVENTION

Gastrointestinal (GI) motility is a coordinated neuromuscular process that transports nutrients through the digestive system. C. Scarpignato, "Pharmacological Stimulation of Gastrointestinal Motility: Where We Are And Where Are We Going?" *Dig. Dis.*, 15: 112 (1997). Impaired (i.e., slowed) motility of the gastrointestinal system, which can be involved in gastroesophageal reflux disease, gastroparesis (e.g., diabetic and postsurgical), irritable bowel syndrome and constipation, is one of the largest health care burdens of industrialized nations. S. D. Feighner et al., "Receptor for Motilin Identified in the Human Gastrointestinal System," *Science*, 284: 2184-2188 (Jun. 25, 1999).

In view of the above, an effective, physiological way to stimulate motility of the gastrointestinal system is highly desirable.

SUMMARY OF THE INVENTION

The present invention relates to a method of stimulating the motility of the gastrointestinal system in a subject in need thereof, wherein the subject suffers from maladies (i.e., disorders or diseases) of the gastrointestinal system. The method comprises administering to a subject in need thereof a therapeutically effective amount of a growth hormone secretagogue compound or a pharmaceutically acceptable salt, hydrate or solvate thereof.

In one embodiment, stimulation of gastrointestinal motility is used in a method of treating opioid induced constipation in a subject in need thereof comprising administering a therapeutically effective amount of a growth hormone secretagogue compound or a pharmaceutically acceptable salt, hydrate or solvate thereof. In one embodiment, the subject is using opioids for post-surgical pain management. In another embodiment, the subject is using opioids for chronic pain management. Suitable opioids included, but are not limited to, percocet, morphine, vicoden, methadone, oxycodone and fentanyl. In a particular embodiment, the growth hormone secretagogue is represented by Formulas I-V, or a pharmaceutically acceptable salt, hydrate or solvate thereof.

In another embodiment, stimulation of gastrointestinal motility is used in a method of treating diabetes related gastroparesis in a subject in need thereof comprising administering a therapeutically effective amount of a growth hormone secretagogue compound. In a particular embodiment, the growth hormone secretagogue is represented by Formulas or a pharmaceutically acceptable salt, hydrate or solvate thereof.

In a further embodiment, stimulation of gastrointestinal motility is used in a method of treating gastroesophageal reflux disease (GERD) in a subject in need thereof comprising administering a therapeutically effective amount of a growth hormone secretagogue compound. In a particular embodiment, the growth hormone secretagogue is represented by Formulas I-V, or a pharmaceutically acceptable salt, hydrate or solvate thereof. In a particular embodiment, the gastroesophageal reflux disease is nocturnal gastroesophageal reflux disease.

In yet another embodiment, stimulation of gastrointestinal motility is used in a method of treating irritable bowel syndrome (IBS) in a subject in need thereof comprising administering a therapeutically effective amount of a growth hormone secretagogue compound. In a particular embodiment, the growth hormone secretagogue is represented by Formulas I-V, or a pharmaceutically acceptable salt, hydrate or solvate thereof. In one embodiment, the irritable bowel syndrome is constipation-predominant irritable bowel syndrome. In another embodiment, the irritable bowel syndrome is alternating constipation/diarrhea irritable bowel syndrome.

In one embodiment, stimulation of gastrointestinal motility is used in a method of treating constipation in a subject in need thereof comprising administering a therapeutically effective amount of a growth hormone secretagogue compound. In a particular embodiment, the growth hormone secretagogue is represented by Formulas I-V, or a pharmaceutically acceptable salt, hydrate or solvate thereof.

In one embodiment, stimulation of gastrointestinal motility is used in a method of treating post-operative ileus in a subject in need thereof comprising administering a therapeutically effective amount of a growth hormone secretagogue compound. In a particular embodiment, the growth hormone secretagogue is represented by Formulas I-V, or a pharmaceutically acceptable salt, hydrate or solvate thereof.

In a particular embodiment, the growth hormone secretagogue is represented by the structural Formula I:

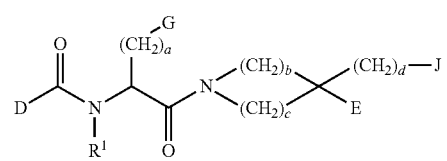

wherein:

$R^1$ is hydrogen, or $C_{1-6}$-alkyl optionally substituted with one or more aryl or hetaryl;

a and d are independently 0, 1, 2 or 3;

b and c are independently 0, 1, 2, 3, 4 or 5, provided that b+c is 3, 4 or 5;

D is $R^2$—NH—$(CR^3R^4)_e$—$(CH_2)_f$-M-$(CHR^5)_g$—$(CH_2)_h$— wherein:

$R^2$, $R^3$, $R^4$ and $R^5$ are independently hydrogen or $C_{1-6}$ alkyl optionally substituted with one or more halogen, amino, hydroxyl, aryl or hetaryl; or $R^2$ and $R^3$ or $R^2$ and $R^4$ or $R^3$ and $R^4$ can optionally form —$(CH_2)_i$—U—$(CH_2)_j$—, wherein i and j are independently 1 or 2 and U is —O—, —S— or a valence bond;

h and f are independently 0, 1, 2, or 3;

g and e are independently 0 or 1;

M is a valence bond, —$CR^6$═$CR^7$-arylene, hetarylene, —O— or —S—;

$R^6$ and $R^7$ are independently hydrogen, or $C_{1-6}$-alkyl optionally substituted with one or more aryl or hetaryl;

G is —O—$(CH_2)_k$—$R^8$,

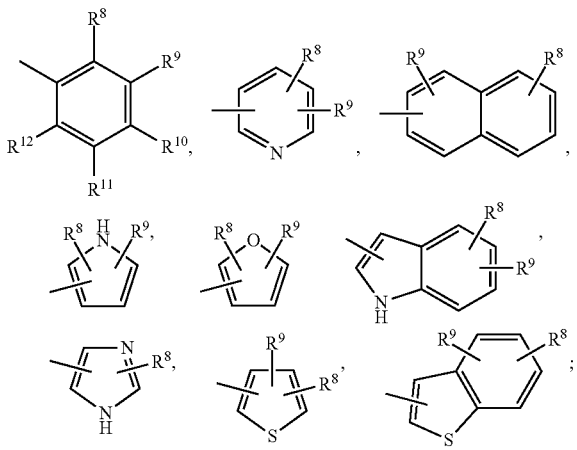

J is —O—$(CH_2)_l$—$R^{13}$,

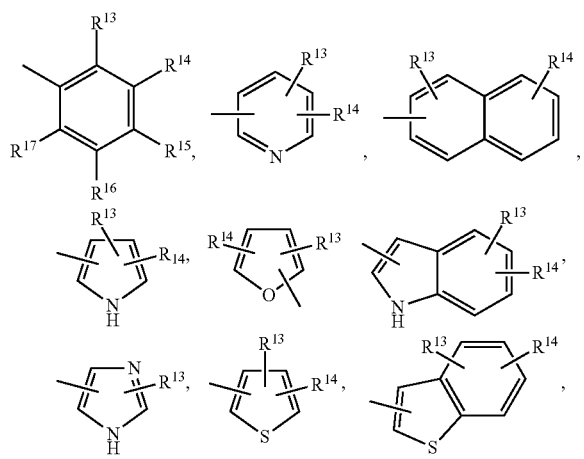

wherein:

$R^8$, $R^9$, $R^{10}$, $R^{11}$, $R^{12}$, $R^{13}$, $R^{14}$, $R^{15}$, $R^{16}$ and $R^{17}$ are independently are hydrogen, halogen, aryl, hetaryl, $C_{1-6}$-alkyl or $C_{1-6}$-alkoxy;

k and l are independently 0, 1 or 2;

E is —$CONR^{18}R^{19}$, —$COOR^{19}$, —$(CH_2)_m$—$NR^{18}SO_2R^{20}$, —$(CH_2)_m$—$NR^{18}$—$COR^{20}$, —$(CH_2)_m$—$OR^{19}$, —$(CH_2)_m$—$OCOR^{20}$, —$CH(R^{18})R^{19}$, —$(CH_2)_m$—$NR^{18}$—CS—$NR^{21}$ or $(CH_2)_m$—$NR^{18}$—CO—$NR^{19}R^{21}$; or

E is —$CONR^{22}$ $NR^{23}R^{24}$, wherein $R^{22}$ is hydrogen, $C_{1-6}$-alkyl optionally substituted with one or more aryl or hetaryl, or aryl or hetaryl optionally substituted with one or more $C_{1-6}$-alkyl; $R^{23}$ is $C_{1-6}$-alkyl optionally substituted with one or more aryl or hetaryl, or $C_{1-7}$-acyl; and $R^{24}$ is hydrogen, $C_{1-6}$-alkyl optionally substituted with one or more aryl or hetaryl; or aryl or hetaryl optionally substituted with one or more $C_{1-6}$-alkyl; or $R^{22}$ and $R^{23}$ together with the nitrogen atoms to which they are attached can form a heterocyclic system optionally substituted with one or more $C_{1-6}$-alkyl, halogen, amino, hydroxyl, aryl or hetaryl; or $R^{22}$ and $R^{24}$ together with the nitrogen atoms to which they are attached can form a heterocyclic system optionally substituted with one or more $C_{1-6}$-alkyl, halogen, amino, hydroxyl, aryl or hetaryl; or $R^{23}$ and $R^{24}$ together with the nitrogen atom to which they are attached can form a heterocyclic system optionally substituted with one or more $C_{1-6}$-alkyl, halogen, amino, hydroxyl, aryl or hetaryl;

wherein m is 0, 1, 2 or 3, $R^{18}$, $R^{19}$ and $R^{21}$ independently are hydrogen or $C_{1-6}$-alkyl optionally substituted with halogen, —$N(R^{25})R^{26}$, wherein $R^{25}$ and $R^{26}$ are independently hydrogen or $C_{1-6}$ alkyl; hydroxyl, $C_{1-6}$-alkoxy, $C_{1-6}$-alkoxycarbonyl, $C_{1-6}$-alkylcarbonyloxy or aryl; or $R^{19}$ is

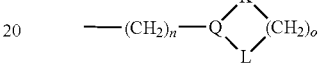

wherein

Q is —CH< or —N<,

K and L are independently —$CH_2$—, —CO—, —O—, —S—, —$NR^{27}$— or a valence bond, where $R^{27}$ is hydrogen or $C_{1-6}$ alkyl;

n and o are independently 0, 1, 2, 3 or 4;

$R^{20}$ is $C_{1-6}$ alkyl, aryl or hetaryl;

or a pharmaceutically acceptable salt thereof;

with the proviso that if M is a valence bond then E is —$CONR^{22}$ $NR^{23}R^{24}$.

The compounds of Formula I are fully described in U.S. Pat. No. 6,303,620 to Hansen, et al., the entire content of which is hereby incorporated by reference.

In another embodiment, the growth hormone secretagogue of Formula I is more specifically represented by the structural Formula II:

II

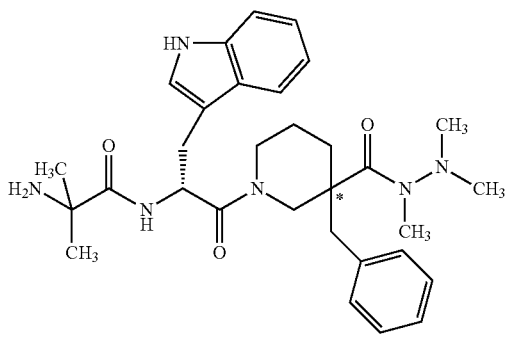

or a pharmaceutically acceptable salt, solvate or hydrate thereof.

The compounds of Formula II are fully described in U.S. Pat. No. 6,303,620 to Hansen, et al., the entire content of which is hereby incorporated by reference.

In yet another embodiment, the growth hormone secretagogue is represented by the structural Formula III:

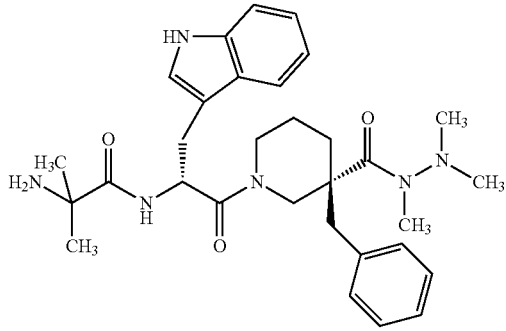

III or a pharmaceutically acceptable salt, solvate or hydrate thereof.

The compound of Formula III is fully described in U.S. Pat. No. 6,303,620 to Hansen, et al., the entire content of which is hereby incorporated by reference. The chemical name of the compound of Formula III is 2-Amino-N-{(1R)-2-[3-benzyl-3-(N,N',N'-trimethylhydrazinocarbonyl)piperidin-1-yl]-1-((1H-indol-3-yl)-2-oxoethyl}-2-methylpropionamide, and is referred to herein as RC-1291.

In a specific embodiment, the growth hormone secretagogue is represented by the structural Formula IV:

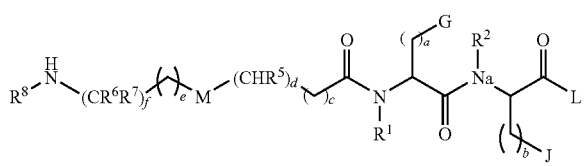

IV wherein
$R^1$ is hydrogen or $C_{1-6}$-alkyl;
$R^2$ is hydrogen or $C_{1-6}$-alkyl;
L is

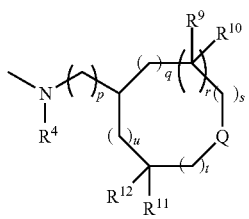

wherein
$R^4$ is hydrogen or $C_{1-6}$ alkyl;
p is 0 or 1;
q, s, t, u are independently 0, 1, 2, 3, or 4;
r is 1;
the sum q+r+s+t+u is 0, 1, 2, 3, or 4;
$R^9$, $R^{19}$, $R^{11}$, and $R^{12}$ are independently hydrogen or $C_{1-6}$ alkyl;

Q is >N—$R^{13}$ or

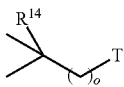

wherein:
o is 0, 1 or 2;
T is —N($R^{15}$)($R^{16}$) or hydroxyl;
$R^{13}$, $R^{15}$, and $R^{16}$ are independently hydrogen or $C_{1-6}$ alkyl;
$R^{14}$ is hydrogen, aryl or hetaryl;
Or L is

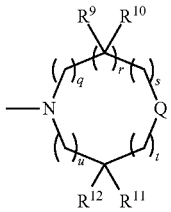

wherein
p is 0 or 1;
q, s, t, u are independently 0, 1, 2, 3, or 4;
r is 0 or 1;
the sum q+r+s+t+u is 0, 1, 2, 3, or 4;
$R^9$, $R^{10}$, $R^{11}$, and $R^{12}$ are independently hydrogen or $C_{1-6}$ alkyl;
Q is >N—$R^{13}$ or

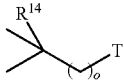

wherein
o is 0, 1, or 2;
T is —N($R^{15}$)($R^{16}$) or hydroxyl;
$R^{13}$, $R^{15}$, and $R^{16}$ are independently from each other hydrogen or $C_{1-6}$ alkyl;
$R^{14}$ is hydrogen, aryl, or hetaryl;
G is —O—($C_2$)—$R^{17}$,

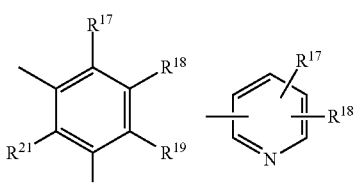

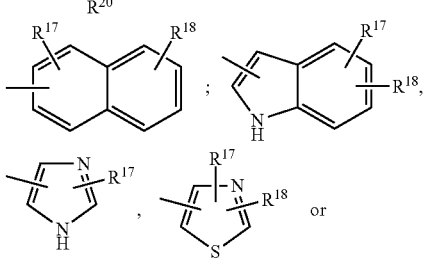

or

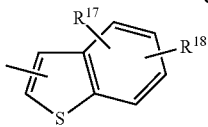

wherein:
$R^{17}$, $R^{18}$, $R^{19}$, $R^{20}$ and $R^{21}$ independently are hydrogen, halogen, aryl, hetaryl, $C_{1-6}$-alkyl or $C_{1-6}$-alkoxy;
K is 0, 1 or 2;
J is —O—$(CH_2)_f$—$R^{22}$, wherein:
$R^{22}$, $R^{23}$, $R^{24}$, $R^{25}$ and $R^{26}$ independently are hydrogen, halogen, aryl, hetaryl, $C_{1-6}$-alkyl or $C_{1-6}$-alkoxy;
l is 0, 1 or 2;
a is 0, 1, or 2;
b is 0, 1, or 2;
c is 0, 1, or 2;
d is 0 or 1;
e is 0, 1, 2, or 3;
f is 0 or 1;
$R^5$ is hydrogen or $C_{1-6}$-alkyl optionally substituted with one or more hydroxyl, aryl or hetaryl;
$R^6$ and $R^7$ are independently hydrogen or $C_{1-6}$-alkyl, optionally substituted with one or more halogen, amino, hydroxyl, aryl, or hetaryl;
$R^8$ is hydrogen or $C_{1-6}$-alkyl, optionally substituted with one or more halogen, amino, hydroxyl, aryl, or hetaryl;
$R^6$ and $R^7$ or $R^6$ and $R^8$ or $R^7$ and $R^8$ can optionally form —$(CH_2)_i$—U—$(CH_2)_j$—, wherein i and j independently are 1, 2 or 3 and U is —O—, —S—, or a valence bond;
M is arylene, hetarylene, —O—, —S— or —$CR^{27}$=$CR^{28}$—;
$R^{27}$ and $R^{28}$ are independently hydrogen or $C_{1-6}$-alkyl, optionally substituted with one or more aryl or hetaryl;
or a pharmaceutically acceptable salt thereof.

The compounds of Formula IV are fully described in Published International Application No. WO 00/01726 to Peschke, et al., the entire content of which is hereby incorporated by reference.

In another embodiment, the growth hormone secretagogue of Formula IV is more specifically represented by the structural Formula V:

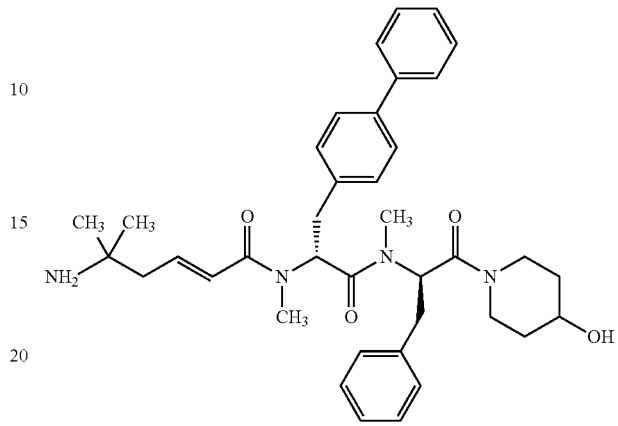

or a pharmaceutically acceptable salt, solvate or hydrate thereof.

The chemical name of the compound of Formula V is (2E)-5-Amino-5-methylhex-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide, referred to herein as RC-1139.

The compound of Formula V is fully described in Published International Application No. WO 00/01726 to Peschke, et al., the entire content of which is hereby incorporated by reference.

Figure 1:
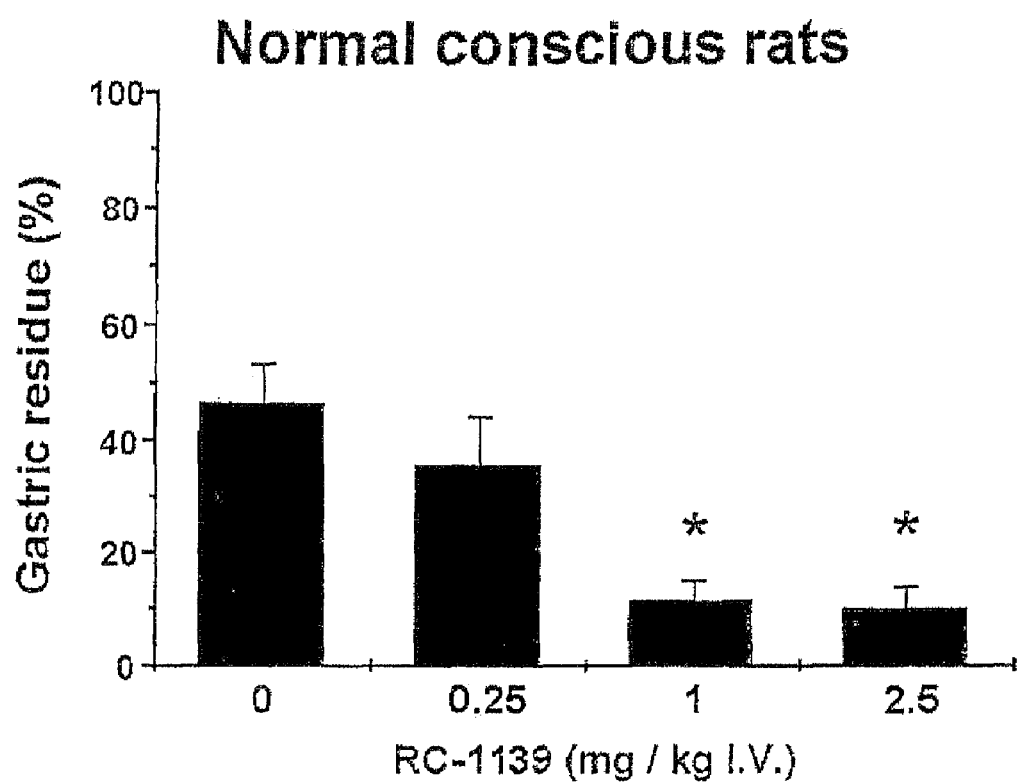
FIG. 1 is a bar graph of percentage of gastric emptying for normal rats administered saline or RC-1139 at a dose of 0.25 mg/kg, 1.0 mg/kg or 2.5 mg/kg. The results demonstrate a statistically significant decrease in gastric residue at 1.0 mg/kg and 2.5 mg/kg of RC-1139 showing a dose-related acceleration of gastric emptying.

The foregoing and other objects, features and advantages of the invention will be apparent from the following more particular description of preferred embodiments of the invention.

DETAILED DESCRIPTION OF THE INVENTION

The present invention relates to a method of stimulating the motility of the gastrointestinal system in a subject in need thereof, wherein the subject suffers from maladies (i.e., disorders or diseases) of the gastrointestinal system. The method comprises administering to a subject in need thereof a therapeutically effective amount of a growth hormone secretagogue compound or a pharmaceutically acceptable salt, hydrate or solvate thereof. In a particular embodiment, the growth hormone secretagogue is a compound represented by any of Formulas I-XVI, or a pharmaceutically acceptable salt, hydrate or solvate thereof.

In one embodiment, stimulation of gastrointestinal motility is used in a method of treating opioid induced constipation in a subject in need thereof comprising administering a therapeutically effective amount of a growth hormone secretagogue compound or a pharmaceutically acceptable salt, hydrate or solvate thereof. In one embodiment, the subject is using opioids for post-surgical pain management. In another embodiment, the subject is using opioids for chronic pain management. Suitable opioids include, but are not limited to, percocet, morphine, vicoden, methadone, oxycodone, and fentanyl. In a particular embodiment, the growth hormone secretagogue is a compound represented by any of Formulas I-XVI, or a pharmaceutically acceptable salt, hydrate or solvate thereof.

In another embodiment, stimulation of gastrointestinal motility is used in a method of treating diabetes related gastroparesis in a subject in need thereof comprising administering a therapeutically effective amount of a growth hormone secretagogue compound. In a particular embodiment, the growth hormone secretagogue is a compound represented by any of Formulas I-XVI, or a pharmaceutically acceptable salt, hydrate or solvate thereof.

In a further embodiment, stimulation of gastrointestinal motility is used in a method of treating gastroesophageal reflux disease (GERD) in a subject in need thereof comprising administering a therapeutically effective amount of a growth hormone secretagogue compound. In a particular embodiment, the growth hormone secretagogue is a compound represented by any of Formulas I-XVI, or a pharmaceutically acceptable salt, hydrate or solvate thereof is administered. In a particular embodiment, the gastroesophageal reflux disease is nocturnal gastroesophageal reflux disease.

In yet another embodiment, stimulation of gastrointestinal motility is used in a method of treating irritable bowel syndrome (IBS) in a subject in need thereof comprising administering a therapeutically effective amount of a growth hormone secretagogue compound. In a particular embodiment, the growth hormone secretagogue is a compound represented by any of Formulas I-XVI, or a pharmaceutically acceptable salt, hydrate or solvate thereof. In a particular embodiment, the irritable bowel syndrome is constipation-predominant irritable bowel syndrome. In one embodiment the irritable bowel syndrome is alternating constipation/diarrhea irritable bowel syndrome.

In one embodiment, stimulation of gastrointestinal motility is used in a method of treating constipation in a subject in need thereof comprising administering a therapeutically effective amount of a growth hormone secretagogue compound. In a particular embodiment, the growth hormone secretagogue is a compound represented by any of Formulas I-XVI, or a pharmaceutically acceptable salt, hydrate or solvate thereof.

In one embodiment, stimulation of gastrointestinal motility is used in a method of treating post-operative ileus in a subject in need thereof comprising administering a therapeutically effective amount of a growth hormone secretagogue compound. In a particular embodiment, the growth hormone secretagogue is represented by a compound represented by any of Formulas I-XVI, or a pharmaceutically acceptable salt, hydrate or solvate thereof.

Opioid Induced Constipation

Use of opioid analgesics to relieve chronic pain can cause effects on organs outside the targets in the central nervous system. For example, the opioid action can slow stomach emptying and inhibit bowel movement. The increased time of fecal contents in the intestines results in excessive absorption of water and sodium from fecal contents, resulting in harder, drier stools and constipation, afflicting approximately 90% of individuals on analgesic pain killers. For chronic pain patients on opioid medications, the resulting constipation can be a dose limiting side-effect. In addition, analgesics used for post-surgical pain management can cause opioid induced constipation. Suitable opioids include, but are not limited to, percocet, morphine, vicoden, methadone, oxycodone and fentanyl, or any combination thereof.

In one embodiment, the method of treating opioid induced constipation comprises co-administering a growth hormone secretagogue compound with a therapeutically effective amount of a peripherally acting opioid antagonist, a laxative, or any combination thereof. Suitable peripherally acting opioid antagonists include, but are not limited to, methylnaltrexone, naltrexone, nalmefene, naloxone and alvimopan or any combination thereof. Suitable laxatives include, but are not limited to bulk forming laxatives, lubricant laxatives, stool softeners, or any combination thereof.

Constipation

Constipation is a condition in which a person has uncomfortable or infrequent bowel movements. A person with constipation produces hard stools that can be difficult to pass. The person also can feel as though the rectum has not been completely emptied. Acute constipation begins suddenly and noticeably. Chronic constipation, on the other hand, can begin insidiously and persist for months or years.

The effectiveness of a candidate growth hormone secretagogue compound in treating constipation can be assessed, for example, using a rat cathartic colon model in which constipation is induced by feeding rats a contact laxative such as phenolphthalein or rhubarb (see, e.g., Liu et al., World J. Gastroenterol. 10:1672-1674 (2004)). After the induction of cathartic colon, constipation is estimated as the number or weight of fecal pellets per unit time (e.g., Nakamura et al., J. Nutr. Sci. Vitaminol. 47:367-372 (2001)) or using a gastrointestinal transit time assay such as the charcoal meal test (Singh et al., Eur. J. Pharmacol. 307:283-289 (1996)). Rats with cathartic colon show decreased fecal output or increased gastrointestinal transit time compared to control rats. The administration of a growth hormone secretagogue compound which is effective at treating constipation increases the number or weight of fecal pellets or decreases gastrointestinal transit time in the rat cathartic colon model. An effective dose of growth hormone secretagogue for treating constipation can be in the range of 0.1 to 100 mg/kg, preferably in the range of 1 to 20 mg/kg, and more preferably in the range of 2 to 10 mg/kg.

In one embodiment, the method of treating constipation comprises co-administering a growth hormone secretagogue compound with a therapeutically effective amount of a laxative. Suitable laxatives include, but are not limited to, bulk forming laxatives, lubricant laxatives, stool softeners, or any combination thereof.

Post-Operative Ileus

It is well established that the motility of the gastrointestinal (GI) tract is temporarily impaired after surgery. The effect that an abdominal operation has on gastrointestinal motility is generally referred to as "postoperative ileus," a term denoting disruption of the normal coordinated movements of the gut, resulting in failure of the propulsion of intestinal contents. Ileus has also been defined as a functional, nonmechanical obstruction of the bowel. The term "post-operative" ileus refers to delay in normal gastric and colonic emptying.

In one embodiment, the method of treating post-operative ileus comprises co-administering a growth hormone secretagogue compound with a therapeutically effective amount of a dopamine antagonist. Suitable dopamine antagonists include, but are not limited to, bethanecol, metoclopramide, domperidone, amisulpride, clebopride, mosapramine, nemonapride, remoxipride, risperidone, sulpiride, sultopride and ziprasidone, or any combination thereof.

Irritable Bowel Syndrome

Irritable bowel syndrome (IBS) is a functional disorder effecting motility of the entire gastrointestinal tract that can produce abdominal pain, constipation, and/or diarrhea. The impaired movement of the digestive tract in IBS is not accompanied by a change in physical structure, such as inflammation or tumors. The symptoms of IBS are thought to be related to abnormal muscle contractions in any part of the intestines.

In this syndrome, the gastrointestinal tract is especially sensitive to gastrointestinal stimuli. Stress, diet, drugs, hormones, or minor irritants can cause the gastrointestinal tract to contract abnormally. There are different types of IBS: constipation-predominant, diarrhea-predominant and alternating constipation-predominant/diarrhea-predominant IBS.

The effectiveness of a candidate growth hormone secretagogue compound in treating IBS can be assessed, for example, using a rat model in which colitis is induced in rats by intracolonic installation of 4% acetic acid (see, e.g., La et al., World J. Gastroenterol. 9:2791-2795 (2003)). After the colitis has subsided (e.g., about seven days after acetic acid treatment), the rats are subjected to a restraint stress test, and stress-induced fecal output is measured. Rats that have undergone colitis induction show increased stress-induced fecal output compared to control rats. The administration of a growth hormone secretagogue compound which is effective at treating IBS reduces the amount of stress-induced defecation in the rat colitis model. An effective dose of growth hormone secretagogue for treating IBS can be in the range of 0.1 to 100 mg/kg, preferably in the range of 1 to 20 mg/kg, and more preferably in the range of 2 to 10 mg/kg.

In one embodiment, the method of treating IBS comprises co-administering a growth hormone secretagogue compound with a therapeutically effective amount of $H_2$ receptor antagonist; a serotonin 5-$HT_4$ agonist; a laxative; or any combination thereof.

Suitable $H_2$ receptor antagonists include, but are not limited to, nizatidine, ranitidine, famotidine, and cimetidine, rabeprazole, or any combination thereof. Suitable 5-$HT_4$ receptor agonist include, but are not limited to, sumatriptan, rauwolscine, yohimbine, metoclopramide, tegaserod, or any combination thereof. Suitable laxatives include, but are not limited to, bulk forming laxatives, lubricant laxatives, stool softeners, or any combination thereof.

Gastroesophageal Reflux Disorder

Gastroesophageal reflux disease (GERD) is a condition in which gastric stomach contents (e.g., bile salts) back up into the food pipe (esophagus), causing chronic regurgitation of gastric contents from the stomach into the lower esophagus. Commonly known as heartburn, GERD causes esophageal irritation and inflammation.

For people with GERD, the esophageal sphincter (a ring-shaped muscle located at the lower end of the esophagus to prevent stomach contents from going backwards into the esophagus) can fail to carry out its protective duties. Instead of opening only when a person is eating or swallowing, it relaxes and allows digestive juices to reflux into the esophagus and irritate the esophageal lining.

Two types of GERD have been identified, upright or daytime GERD and supine or nocturnal GERD. Nocturnal reflux episodes occur less frequently, but acid clearance is more prolonged. Nocturnal reflux can be associated with the complications of GERD, such as esophageal erosions, ulceration, and respiratory symptoms. An estimated 17 million Americans currently suffer from heartburn and other symptoms of GERD.

The effectiveness of a candidate growth hormone secretagogue compound in treating GERD can be assessed, for example, using a rat model in which GERD is induced in rats by a pyloric ligation surgical procedure (see, e.g., Tugay et al., J. Surg. Res. 115:272-8 (2003)) in conjunction with the rat gastric emptying assay described below (see "Study in a Rat Model" under "Normal Conscious Rats"). The gastric emptying assay can be performed after the rats have recovered from surgery. Sham operated rats can be used as controls. Rats that have undergone pyloric ligation have higher amounts of gastric radioactivity at the end of the assay compared with control rats. The administration of a growth hormone secretagogue compound which is effective at treating GERD reduces the amount of gastric radioactivity at the end of the assay. An effective dose of growth hormone secretagogue for treating GERD can be in the range of 0.1 to 100 mg/kg, preferably in the range of 1 to 20 mg/kg, and more preferably in the range of 2 to 10 mg/kg.

In one embodiment, the method of treating GERD comprises co-administering a growth hormone secretagogue compound with a therapeutically effective amount of $H_2$ receptor antagonist; an antacid; a proton pump inhibitor; or any combination thereof.

The effectiveness of a candidate growth hormone secretagogue compound in treating gastroparesis, including diabetes-induced gastroparesis, can be assessed, for example, using the rat gastric emptying assay described below (see "Study in a Rat Model" under "Normal Conscious Rats"). Rats with diabetes induced using streptozotocin are compared to controls. See, e.g., Rees et al., Diabet. Med. 22:359-70 (2005) for a discussion of various rat models of diabetes. Rats showing diabetes-induced gastroparesis have higher amounts of gastric radioactivity at the end of the assay compared with normal control rats. The administration of a growth hormone secretagogue compound which is effective at treating diabetes-induced gastroparesis reduces the amount of gastric radioactivity at the end of the assay. An effective dose of growth hormone secretagogue for treating diabetes-induced gastroparesis can be in the range of 0.1 to 100 mg/kg, preferably in the range of 1 to 20 mg/kg, and more preferably in the range of 2 to 10 mg/kg. The diabetic rat gastric motility assay can be used to determine an optimum effective dose for a given candidate compound.

Suitable $H_2$ receptor antagonist include, but are not limited to, nizatidine, ranitidine, famotidine, and cimetidine, rabeprazole, or any combination thereof. Suitable antacids include, but are not limited to, aluminum and magnesium hydroxide and combinations thereof. Suitable proton pump inhibitors include, but are not limited to, esomeprazole (NEXIUM®), omeprazole, lansoprazole, pantoprazole, or a combination thereof.

Diabetes Related Gastroparesis

Gastroparesis, also referred to as delayed gastric emptying, is a disorder in which the stomach takes too long to empty its contents. It often occurs in people with type 1 diabetes or type 2 diabetes. Gastroparesis can occur when nerves to the stomach are damaged or stop working. The vagus nerve controls the movement of food through the digestive tract. If the vagus nerve is damaged, the muscles of the stomach and intestines do not work normally, and the movement of food is slowed or stopped. Diabetes can damage the vagus nerve if blood glucose levels remain high over a long period of time. High blood glucose causes chemical changes in nerves and damages the blood vessels that carry oxygen and nutrients to the nerves.

The effectiveness of a candidate growth hormone secretagogue compound in treating gastroparesis, including diabetes-induced gastroparesis, can be assessed, for example, using the rat gastric emptying assay described below (see "Study in a Rat Model" under "Normal Conscious Rats"). Rats with diabetes induced using streptozotocin are compared to controls. See, e.g., Rees et al., Diabet. Med. 22:359-70 (2005) for a discussion of various rat models of diabetes. Rats showing diabetes-induced gastroparesis have higher amounts of gastric radioactivity at the end of the assay compared with normal control rats. The administration of a growth hormone secretagogue compound which is effective at treating diabetes-induced gastroparesis reduces the amount of gastric radioactivity at the end of the assay. An effective dose of growth hormone secretagogue for treating diabetes-induced gastroparesis can be in the range of 0.1 to 100 mg/kg, preferably in the range of 1 to 20 mg/kg, and more preferably in the range of 2 to 10 mg/kg.

In one embodiment, the method of treating diabetes related gastroparesis comprises co-administering a growth hormone secretagogue compound with a therapeutically effective amount of dopamine antagonist. Suitable dopamine antagonists include, but are not limited to, bethanecol, metoclopramide, domperidone, amisulpride, clebopride, mosapramine, nemonapride, remoxipride, risperidone, sulpiride, sultopride and ziprasidone, or any combination thereof.

The invention further relates to pharmaceutical compositions useful for stimulating (i.e., inducing) motility of the gastrointestinal system. The pharmaceutical composition comprises a growth hormone secretagogue and optionally a pharmaceutically acceptable carrier. The pharmaceutical composition can comprise a second amount of a suitable therapeutic agent. A suitable therapeutic agent can be determined based on the condition being treated in the subject.

For example, the pharmaceutical composition can comprise a first amount of a growth hormone secretagogue and a second amount of a laxative when treating constipation. The pharmaceutical composition of the present invention can optionally contain a pharmaceutically acceptable carrier. The growth hormone secretagogue and laxative can each be present in the pharmaceutical composition in a therapeutically effective amount. In another aspect, said first and second amount can together comprise a therapeutically effective amount.

In a particular embodiment, the pharmaceutical composition can comprise a first amount of a growth hormone secretagogue and a second amount of a $H_2$ receptor antagonist. The pharmaceutical composition of the present invention can optionally contain a pharmaceutically acceptable carrier. The growth hormone secretagogue and $H_2$ receptor antagonist can each be present in the pharmaceutical composition in a therapeutically effective amount. In another aspect, said first and second amount can together comprise a therapeutically effective amount.

In another embodiment, the pharmaceutical composition can comprise a first amount of a growth hormone secretagogue and a second amount of a serotonin 5-$HT_4$ agonist. The pharmaceutical composition of the present invention can optionally contain a pharmaceutically acceptable carrier. The growth hormone secretagogue and serotonin 5-$HT_4$ agonist can each be present in the pharmaceutical composition in a therapeutically effective amount. In another aspect, said first and second amount can together comprise a therapeutically effective amount.

In yet another embodiment, the pharmaceutical composition can comprise a first amount of a growth hormone secretagogue and a second amount of an antacid. The pharmaceutical composition of the present invention can optionally contain a pharmaceutically acceptable carrier. The growth hormone secretagogue and antacid can each be present in the pharmaceutical composition in a therapeutically effective amount. In another aspect, said first and second amount can together comprise a therapeutically effective amount.

In a particular embodiment, the pharmaceutical composition can comprise a first amount of a growth hormone secretagogue and a second amount of an opioid antagonist. The pharmaceutical composition of the present invention can optionally contain a pharmaceutically acceptable carrier. The growth hormone secretagogue and opioid antagonist can each be present in the pharmaceutical composition in a therapeutically effective amount. In another aspect, said first and second amount can together comprise a therapeutically effective amount.

In another embodiment, the pharmaceutical composition can comprise a first amount of a growth hormone secretagogue and a second amount of a proton pump inhibitor. The pharmaceutical composition of the present invention can optionally contain a pharmaceutically acceptable carrier. The growth hormone secretagogue and proton pump inhibitor can each be present in the pharmaceutical composition in a therapeutically effective amount. In another aspect, said first and second amount can together comprise a therapeutically effective amount.

In another embodiment, the pharmaceutical composition can comprise a first amount of a growth hormone secretagogue and a second amount of a motilin receptor agonist. The pharmaceutical composition of the present invention can optionally contain a pharmaceutically acceptable carrier. The growth hormone secretagogue and motilin receptor agonist can each be present in the pharmaceutical composition in a therapeutically effective amount. In another aspect, said first and second amount can together comprise a therapeutically effective amount.

In another embodiment, the pharmaceutical composition can comprise a first amount of a growth hormone secretagogue and a second amount of a dopamine antagonist. The pharmaceutical composition of the present invention can optionally contain a pharmaceutically acceptable carrier. The growth hormone secretagogue and dopamine antagonist can each be present in the pharmaceutical composition in a therapeutically effective amount. In another aspect, said first and second amount can together comprise a therapeutically effective amount.

In another embodiment, the pharmaceutical composition can comprise a first amount of a growth hormone secretagogue and a second amount of a cholinesterase inhibitor. The pharmaceutical composition of the present invention can optionally contain a pharmaceutically acceptable carrier. The growth hormone secretagogue and cholinesterase inhibitor can each be present in the pharmaceutical composition in a therapeutically effective amount. In another aspect, said first and second amount can together comprise a therapeutically effective amount.

In another embodiment, the pharmaceutical composition can comprise a first amount of a growth hormone secretagogue and a second amount of somatostatin. The pharmaceutical composition of the present invention can optionally contain a pharmaceutically acceptable carrier. The growth hormone secretagogue and somatostatin can each be present in the pharmaceutical composition in a therapeutically effective amount. In another aspect, said first and second amount can together comprise a therapeutically effective amount.

In another embodiment, the pharmaceutical composition can comprise a first amount of a growth hormone secretagogue and a second amount of octreotide. The pharmaceutical composition of the present invention can optionally contain a pharmaceutically acceptable carrier. The growth hormone secretagogue and octreotide can each be present in the pharmaceutical composition in a therapeutically effective amount. In another aspect, said first and second amount can together comprise a therapeutically effective amount.

The invention further relates to use of a growth hormone secretagogue compound for the manufacture of a medicament for stimulating (i.e., inducing) the motility of the gastrointestinal system.

Growth Hormone Secretagogues/Ghrelin Agonists

As used herein, the terms growth hormone secretagogue compound and ghrelin agonist are synonymous. A growth hormone secretagogue or ghrelin agonist therefore refers to a substance (e.g., a molecule, a compound) which promotes (induces or enhances) at least one function characteristic of a growth hormone secretagogue receptor (GHS receptor) also referred to in the art as a ghrelin receptor. In one embodiment, the growth hormone secretagogue compound or ghrelin agonist binds the GHS receptor or ghrelin receptor (i.e., is a ghrelin or GHS receptor agonist) and induces the secretion of growth hormone. A compound having GHS receptor agonist activity (e.g., a GHS receptor or ghrelin receptor agonist) can be identified and activity assessed by any suitable method. For example, the binding affinity of a GHS receptor agonist to the GHS receptor can be determined employing receptor binding assays and growth hormone stimulation can be assessed as described in Published International Application No. WO 00/01726, incorporated herein by reference.

GHS receptors and ghrelin receptors are expressed in the hypothalamus, pituitary and pancreas, among other tissues. Activation of these receptors in the pituitary induces the secretion of growth hormone. In addition to inducing the secretion of growth hormone, recent studies have shown the growth hormone secretagogues can increase appetite and body weight. At typical doses, growth hormone secretagogues are also known to induce the secretion of IGF-1. In a particular embodiment, the growth hormone secretagogue compounds are those described in U.S. Pat. Nos. 6,303,620, 6,576,648, 5,977,178, 6,566,337, 6,083,908, 6,274,584 and Published International Application No. WO 00/01726, the entire content of all of which are incorporated herein by reference.

In a particular embodiment, the growth hormone secretagogue is represented by the structural Formula I:

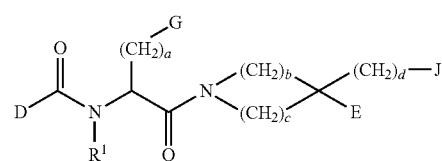

wherein:

$R^1$ is hydrogen, or $C_{1-6}$-alkyl optionally substituted with one or more aryl or hetaryl;

a and d are independently 0, 1, 2 or 3;

b and c are independently 0, 1, 2, 3, 4 or 5, provided that b+c is 3, 4 or 5;

D is $R^2$—NH—$(CR^3R^4)_e$—$(CH_2)_f$-M—$(CHR^5)_g$—$(CH_2)_h$— wherein:

$R^2, R^3, R^4$ and $R^5$ are independently hydrogen or $C_{1-6}$ alkyl optionally substituted with one or more halogen, amino, hydroxyl, aryl or hetaryl; or $R^2$ and $R^3$ or $R^2$ and $R^4$ or $R^3$ and $R^4$ can optionally form —$(CH_2)_i$—U—$(CH_2)_j$—, wherein i and j are independently 1 or 2 and U is —O—, —S— or a valence bond;

h and f are independently 0, 1, 2, or 3;

g and e are independently 0 or 1;

M is a valence bond, —$CR^6$=$CR^7$, arylene, hetarylene, —O— or —S—;

$R^6$ and $R^7$ are independently hydrogen, or $C_{1-6}$-alkyl optionally substituted with one or more aryl or hetaryl;

G is —$O(CH_2)_k$—$R^8$,

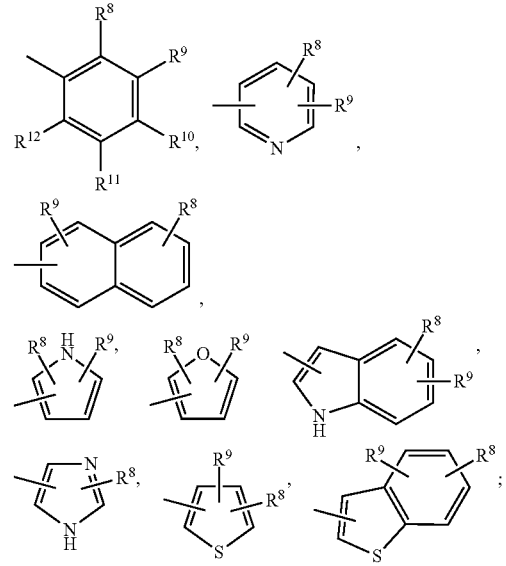

J is —O—$(CH_2)_l$—$R^{13}$,

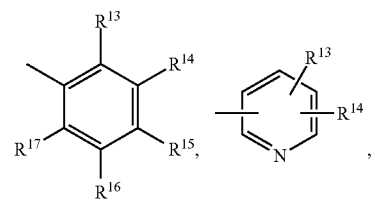

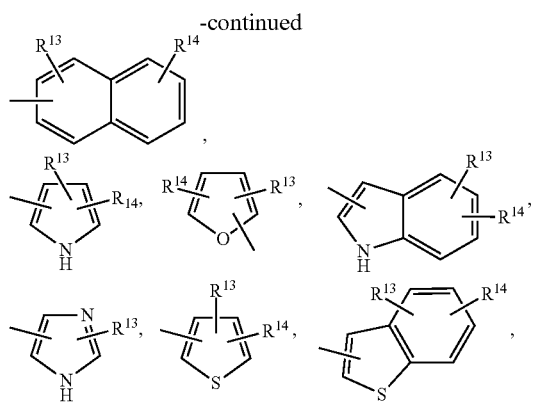

wherein:
R$^8$, R$^9$, R$^{10}$, R$^{11}$, R$^{12}$, R$^{13}$, R$^{14}$, R$^{15}$, R$^{16}$ and R$^{17}$ independently are hydrogen, halogen, aryl, hetaryl, C$_{1-6}$-alkyl or C$_{1-6}$-alkoxy;

k and l are independently 0, 1 or 2;

E is —CONR$^{18}$R$^{19}$, —COOR$^{19}$, —(CH$_2$)$_m$—NR$^{18}$SO$_2$R$^{20}$, —(CH$_2$)$_m$—NR$^{18}$—COR$^{20}$, —(CH$_2$)$_m$—OR$^{19}$, —(CH$_2$)$_m$—OCOR$^{20}$, —CH(R$^{18}$)R$^{19}$, —(CH$_2$)$_m$—NR$^{18}$—CS—NR$^{19}$R$^{21}$ or (CH$_2$)$_m$—NR$^{18}$—CO—NR$^{19}$R$^{21}$; or

E is —CONR$^{22}$NR$^{23}$R$^{24}$, wherein R$^{22}$ is hydrogen, C$_{1-6}$-alkyl optionally substituted with one or more aryl or hetaryl, or aryl or hetaryl optionally substituted with one or more C$_{1-6}$-alkyl; R$^{23}$ is C$_{1-6}$-alkyl optionally substituted with one or more aryl or hetaryl, or C$_{1-7}$-acyl; and R$^{24}$ is hydrogen, C$_{1-6}$-alkyl optionally substituted with one or more aryl or hetaryl; or aryl or hetaryl optionally substituted with one or more C$_{1-6}$-alkyl; or R$^{22}$ and R$^{23}$ together with the nitrogen atoms to which they are attached can form a heterocyclic system optionally substituted with one or more C$_{1-6}$-alkyl, halogen, amino, hydroxyl, aryl or hetaryl; or R$^{22}$ and R$^{24}$ together with the nitrogen atoms to which they are attached can form a heterocyclic system optionally substituted with one or more C$_{1-6}$-alkyl, halogen, amino, hydroxyl, aryl or hetaryl; or R$^{23}$ and R$^{24}$ together with the nitrogen atom to which they are attached can form a heterocyclic system optionally substituted with one or more C$_{1-6}$-alkyl, halogen, amino, hydroxyl, aryl or hetaryl;

wherein m is 0, 1, 2 or 3,

R$^{18}$, R$^{19}$ and R$^{21}$ independently are hydrogen or C$_{1-6}$-alkyl optionally substituted with halogen, —N(R$^{25}$)R$^{26}$, wherein R$^{25}$ and R$^{26}$ are independently hydrogen or C$_{1-6}$ alkyl; hydroxyl, C$_{1-6}$-alkoxy, C$_{1-6}$-alkoxycarbonyl, C$_{1-6}$-alkylcarbonyloxy or aryl; or R$^{19}$ is

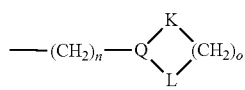

wherein
Q is —CH< or N<,
K and L are independently —CH$_2$, —CO—, —O—, —S—, —NR$^{27}$— or a valence bond, where R$^{27}$ is hydrogen or C$_{1-6}$ alkyl;
n and o are independently 0, 1, 2, 3 or 4;
R$^{20}$ is C$_{1-6}$ alkyl, aryl or hetaryl;
or a pharmaceutically acceptable salt thereof;
with the proviso that if M is a valence bond then E is CONR$^{22}$NR$^{23}$R$^{24}$.

In another embodiment, R$^1$ is C$_{1-6}$-alkyl. In yet another embodiment, a is 1.

In one embodiment, d is 1. In another embodiment, b+c is 4.

In yet another embodiment, D is

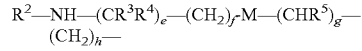

wherein
R$^2$, R$^3$, R$^4$ and R$^5$ are independently hydrogen or C$_{1-6}$ alkyl optionally substituted with a halogen, amino, hydroxyl, aryl or hetaryl; or
R$^2$ and R$^3$ or R$^2$ and R$^4$ or R$^3$ and R$^4$ can optionally form —(CH$_2$)$_i$—U—(CH$_2$)$_j$—, wherein i and j are independently 1 or 2 and U is —O—, —S— or a valence bond;
h and f are independently 0, 1, 2, or 3;
g and e are independently 0 or 1;
M is —CR$^6$═CR$^7$ arylene, hetarylene, —O— or —S—; and
R$^6$ and R$^7$ are independently hydrogen, or C$_{1-6}$-alkyl.

In a further embodiment, D is

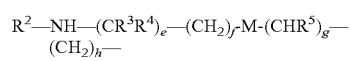

wherein:
R$^2$, R$^3$, R$^4$ and R$^5$ are independently hydrogen or C$_{1-6}$ alkyl optionally substituted with a halogen, amino, hydroxyl, aryl or hetaryl; or
R$^2$ and R$^3$ or R$^2$ and R$^4$ or R$^3$ and R$^4$ can optionally form —(CH$_2$)$_i$—U—(CH$_2$)$_j$—, wherein i and j are independently 1 or 2 and U is —O—, —S— or a valence bond; h and f are independently 0, 1, 2, or 3; g and e are independently 0 or 1; M is a valence bond.

In another embodiment, G is

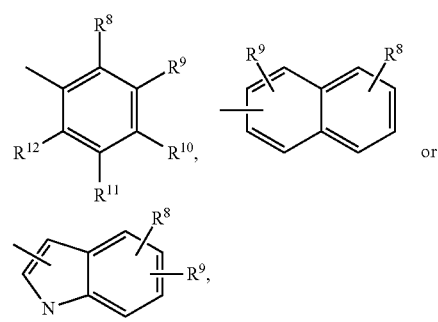

wherein:
R$^8$, R$^9$, R$^{10}$, R$^{11}$ and R$^{12}$ independently are hydrogen, halogen, aryl, hetaryl, C$_{1-6}$-alkyl or C$_{1-6}$ alkoxy; and k is 0, or 2.

In yet another embodiment, J is

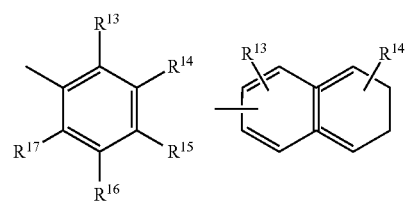

wherein:

$R^{13}$, $R^{14}$, $R^{15}$ $R^{16}$ and $R^{17}$ independently are hydrogen, halogen, aryl, hetaryl, $C_{1-6}$-alkyl or $C_{1-6}$-alkoxy.

In one embodiment, E is —$CONR^{18}R^{19}$, —$COOR^{19}$ or $(CH_2)_m$—O—$R^{19}$, wherein:

m is 0, 1, 2 or 3;

$R^{18}$ and $R^{19}$ independently are hydrogen or $C_{1-6}$-alkyl optionally substituted by halogen, —$N(R^{25})R^{26}$ wherein $R^{25}$ and $R^{26}$ are independently hydrogen or $C_{1-6}$ alkyl; hydroxyl, $C_{1-6}$-alkoxy, $C_{1-6}$-alkoxycarbonyl, $C_{1-6}$-alkylcarbonyloxy or aryl.

In another embodiment, E is —$CONR^{22}$ $NR^{23}R^{24}$ wherein:

$R^{22}$ is hydrogen, $C_{1-6}$-alkyl optionally substituted with an aryl or hetaryl, or aryl or hetaryl optionally substituted with a $C_{1-6}$-alkyl;

$R^{23}$ is $C_{1-6}$-alkyl optionally substituted with one or more aryl or hetaryl, or $C_{1-7}$-acyl; and $R^{24}$ is hydrogen, $C_{1-6}$-alkyl optionally substituted with an aryl or hetaryl; or aryl or hetaryl optionally substituted with a $C_{1-6}$-alkyl; or $R^{22}$ and $R^{23}$ together with the nitrogen atoms to which they are attached can form a heterocyclic system optionally substituted with a $C_{1-6}$-alkyl, halogen, amino, hydroxyl, aryl or hetaryl; or $R^{22}$ and $R^{24}$ together with the nitrogen atoms to which they are attached can form a heterocyclic system optionally substituted with a $C_{1-6}$-alkyl, halogen, amino, hydroxyl, aryl or hetaryl; or $R^{23}$ and $R^{24}$ together with the nitrogen atom to which they are attached can form a heterocyclic system optionally substituted with a $C_{1-6}$-alkyl, halogen, amino, hydroxyl, aryl or hetaryl.

In a specific embodiment, the growth hormone secretagogue is represented by the structural Formula II:

II

In a preferred embodiment, the compound of Formula II has the (R) configuration at the chiral carbon designated by the asterisk (*) in Formula II. The chemical name of the compound of Formula II having the (R) configuration at the designated chiral carbon is: 2-Amino-N-{(1R)-2-[3-benzyl-3-(N,N',N'-trimethylhydrazinocarbonyl)piperidin-1-yl]-1-((1H-indol-3-yl)-2-oxoethyl}-2-methylpropionamide. Represented by structural Formula III:

III and pharmaceutically acceptable salts thereof.

In a specific embodiment, the growth hormone secretagogue is represented by the structural Formula IV:

IV wherein
$R^1$ is hydrogen or $C_{1-6}$-alkyl;
$R^2$ is hydrogen or $C_{1-6}$-alkyl;
L is wherein
$R^4$ is hydrogen or $C_{1-6}$ alkyl;
p is 0 or 1;
q, s, t, u are independently 0, 1, 2, 3, or 4;
r is 1;
the sum q+r+s+t+u is 0, 1, 2, 3, or 4;
$R^9$, $R^{10}$, $R^{11}$, and $R^{12}$ are independently hydrogen or $C_{1-6}$ alkyl;
Q is >N—$R^{13}$ or wherein:
o is 0, 1 or 2;
T is —$N(R^{15})(R^{16})$ or hydroxyl;
$R^{13}$, $R^{15}$, and $R^{16}$ are independently hydrogen or $C_{1-6}$ alkyl;
$R^{14}$ is hydrogen, aryl or hetaryl;

Or L is

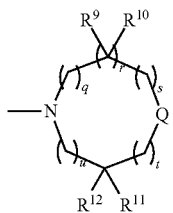

wherein
p is 0 or 1;
q, s, t, u are independently 0, 1, 2, 3, or 4;
r is 0 or 1;
the sum q+r+s+t+u is 0, 1, 2, 3, or 4;
$R^9$, $R^{10}$, $R^{11}$, and $R^{12}$ are independently hydrogen or $C_{1-6}$ alkyl;
Q is >N—$R^{13}$ or

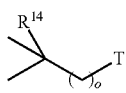

wherein
o is 0, 1, or 2;
T is —N($R^{15}$)($R^{16}$) or hydroxyl;
$R^{13}$, $R^{15}$, and $R^{16}$ are independently from each other hydrogen or $C_{1-6}$ alkyl;
$R^{14}$ is hydrogen, aryl, or hetaryl;
G is —O—(CH$_2$)—$R^{17}$,

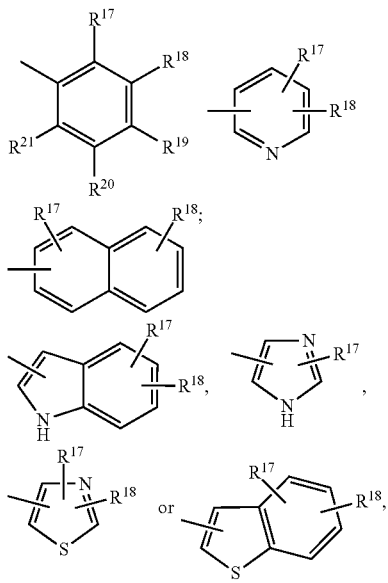

wherein:
$R^{17}$, $R^{18}$, $R^{19}$, $R^{20}$ and $R^{21}$ independently are hydrogen, halogen, aryl, hetaryl, $C_{1-6}$-alkyl or $C_{1-6}$-alkoxy;
K is 0, 1 or 2;
J is —O—(CH$_2$)$_l$—$R^{22}$,

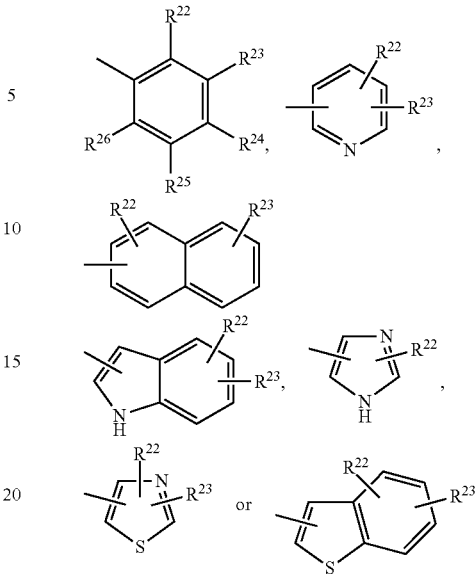

wherein:
$R^{22}$, $R^{23}$, $R^{24}$, $R^{25}$ and $R^{26}$ independently are hydrogen, halogen, aryl, hetaryl, $C_{1-6}$-alkyl or $C_{1-6}$-alkoxy;
l is 0, 1 or 2;
a is 0, 1, or 2;
b is 0, 1, or 2;
c is 0, 1, or 2;
d is 0 or 1;
e is 0, 1, 2, or 3;
f is 0 or 1;
$R^5$ is hydrogen or $C_{1-6}$-alkyl optionally substituted with one or more hydroxyl, aryl or hetaryl;
$R^6$ and $R^7$ are independently hydrogen or $C_{1-6}$-alkyl, optionally substituted with one or more halogen, amino, hydroxyl, aryl, or hetaryl;
$R^8$ is hydrogen or $C_{1-6}$-alkyl, optionally substituted with one or more halogen, amino, hydroxyl, aryl, or hetaryl;
$R^6$ and $R^7$ or $R^6$ and $R^8$ or $R^7$ and $R^8$ can optionally form —(CH$_2$)$_i$—U—(CH$_2$)$_j$—, wherein i and j independently are 1, 2 or 3 and U is —O—, —S—, or a valence bond;
M is arylene, hetarylene, —O—, —S— or —C$R^{27}$=C$R^{28}$—;
$R^{27}$ and $R^{28}$ are independently hydrogen or $C_{1-6}$-alkyl, optionally substituted with one or more aryl or hetaryl;
or a pharmaceutically acceptable salt thereof.

In another embodiment, $R^1$ is $C_{1-6}$-alkyl.
In yet another embodiment, $R^2$ is $C_{1-6}$-alkyl.
In one embodiment, L is

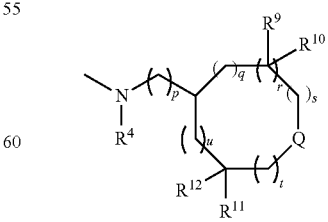

wherein $R^4$ is hydrogen or $C_1$ alkyl;
p is 0 or 1;
q, s, t, u are independently from each other 0, 1, 2, 3 or 4;

r is 0 or 1;
the sum q+r+s+t+u iso, 1, 2, 3, or 4;
$R^9$, $R^{10}$, $R^{11}$, and $R^{12}$ are independently from each other hydrogen or $C_{1-6}$ alkyl;
Q is >N—$R^{13}$ or

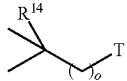

wherein:
o is 0, 1 or 2;
T is —N($R^{15}$)($R^{16}$) or hydroxyl;
$R^{13}$, $R^{15}$, and $R^{16}$ are independently from each other hydrogen or $C_{1-6}$ alkyl; and
$R^{14}$ is hydrogen, aryl or hetaryl.

In another embodiment, L is

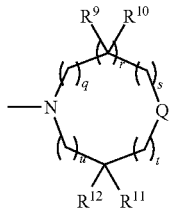

wherein:
q, s, t, u are independently from each other 0, 1, 2, 3 or 4;
r is 0 or 1;
the sum q+r+s+t+u is 0, 1, 2, 3, or 4;
$R^9$, $R^{10}$, $R^{11}$, and $R^{12}$ are independently from each other hydrogen or $C_{1-6}$ alkyl;
Q is >N—$R^{13}$ or

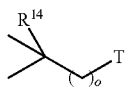

wherein:
o is 0, 1 or 2;
T is —N($R^{15}$)($R^{16}$) or hydroxyl;
$R^{13}$, $R^{15}$, and $R^{16}$ are independently from each other hydrogen or $C_{1-6}$ alkyl; and
$R^{14}$ is hydrogen, aryl or hetaryl.

In yet another embodiment, G is

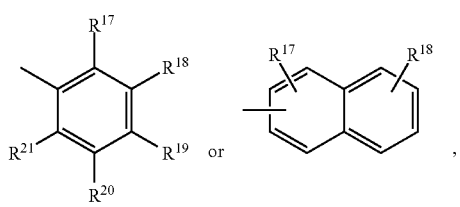

wherein:
$R^{17}$, $R^{18}$, $R^{19}$, $R^{20}$ and $R^{21}$ independently from each other are hydrogen, halogen, aryl, hetaryl, $C_{1-6}$-alkyl or $C_{1-6}$-alkoxy.

In one embodiment, J is

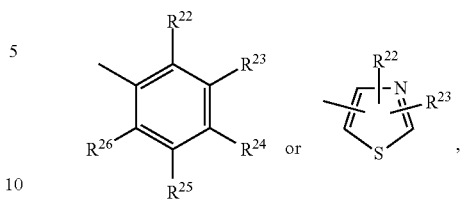

wherein:
$R^{22}$, $R^{23}$, $R^{24}$, $R^{25}$ and $R^{26}$ independently from each other are hydrogen, halogen, aryl, hetaryl, $C_{1-6}$-alkyl or $C_{1-6}$-alkoxy.

In another embodiment, M is arylene or —$CR^{27}$=$CR^{28}$—, wherein $R^{27}$ and $R^{28}$ independently from each other hydrogen or $C_{1-6}$-alkyl, optionally substituted with aryl or hetaryl.

In yet another embodiment, $R^6$ and $R^7$ independently from each other are hydrogen or $C_{1-6}$-alkyl.

In yet another embodiment, $R^6$ and $R^7$ form —$(CH_2)_i$—U—$(CH_2)_j$—, wherein i and j independently from each other are 1, 2 or 3 and U is —O—, —S—, or a valence bond.

In one embodiment, $R^8$ is hydrogen or $C_{1-6}$-alkyl.

In another embodiment, the growth hormone secretagogue compound is represented by the structural Formula V. The chemical name of the compound of Formula V is (2E)-5-Amino-5-methylhex-2-enoic acid N-((1R)-1-{N-[(1R)-1-benzyl-2-(4-hydroxypiperidin-1-yl)-2-oxoethyl]-N-methyl-carbamoyl}-2-(biphenyl-4-yl)ethyl)-N-methylamide, also referred to herein as RC-1139. The RC-1139 is represented by structural Formula V:

V

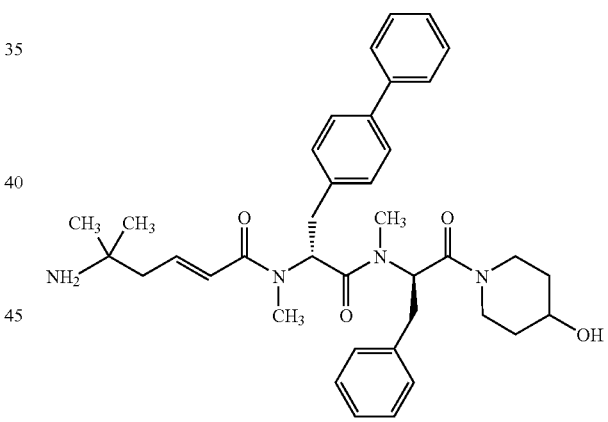

and pharmaceutically acceptable salts thereof.

Other compounds of interest include the following:
1-{(2R)-2-[N-((2E)-5-Amino-5-methylhex-2-enoyl)-N-methylamino]-3-(2-naphthyl)propionyl}-4-benzylpiperidine-4-carboxylic acid methylamide,

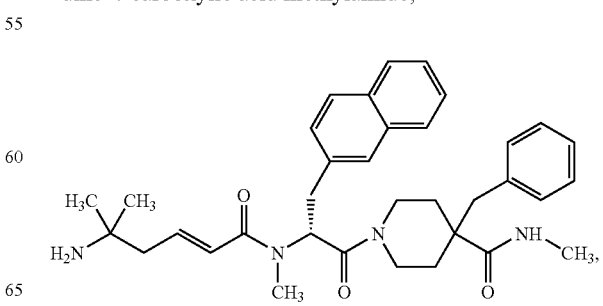

25

1-{(1R)-2-[N-((2E)-5-Amino-3,5-dimethylhex-2-enoyl)-N-methylamino]-3-(2-naphthyl)propionyl}-4-benzylpiperidine-4-carboxylic acid methylamide

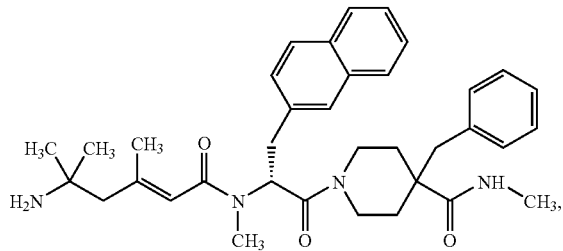

1-{(2R)-2-[N-((2E)-5-Amino-5-methylhex-2-enoyl)-N-methylamino]-3-(biphenyl-4-yl)propionyl}4-benzylpiperidine-4-carboxylic acid methylamide

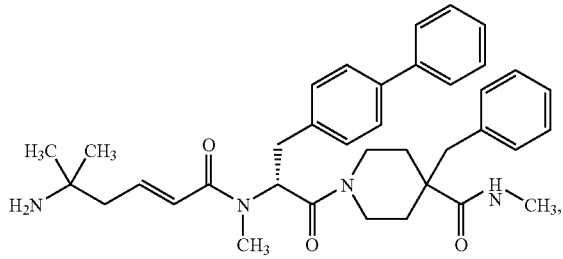

1-{(2R)-2-[N-((2E)-5-Amino-3,5-dimethylhex-2-enoyl)-N-methylamino]-3-(biphenyl-4-yl)propionyl}-4-benzylpiperidine-4-carboxylic acid methylamide

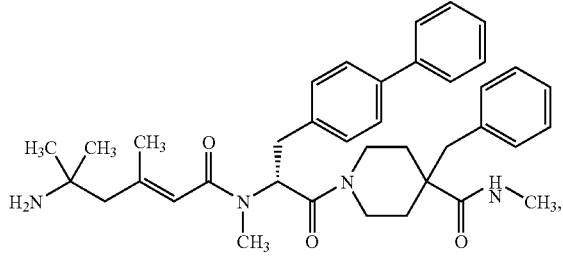

1-((2R)-2-{N-[(2E)-4-(1-Aminocyclobutyl)but-2-enoyl]-N-methylamino}-3-(biphenyl-4-yl)propionyl)-4-benzylpiperidine-4-carboxylic acid methylamide

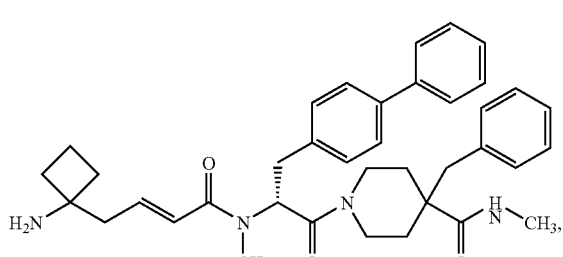

26

2-Amino-N-[(1R)-2-[4-benzyl-4-(N',N'-dimethylhydrazinocarbonyl)piperidin-1-yl]-1-((1H-indol-3-yl)methyl)-2-oxoethyl]-2-methylpropionamide

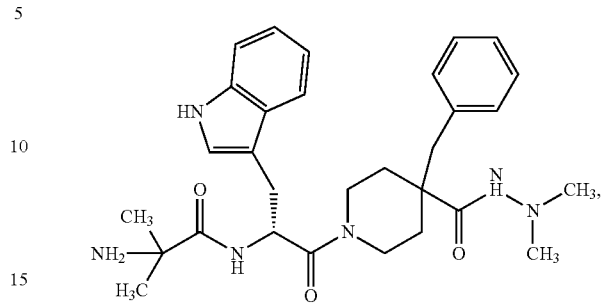

2-Amino-N-{(1R)-2-[(3R)-3-benzyl-3-(N',N'-dimethyl-hydrazinocarbonyl)-piperidin-1-yl]-1-benzyloxymethyl-2-oxo-ethyl}-2-methyl-propionamide

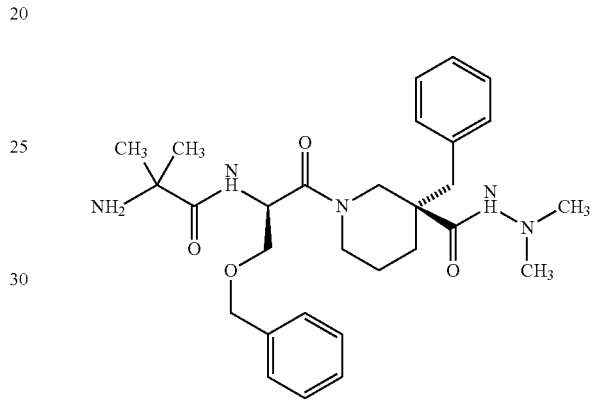

2-Amino-N-[(1R)-2-[(3R)-3-benzyl-3-(N'N'-dimethylhydrazinocarbonyl)-piperidin-1-yl]-1-((1H-indol-3-yl)methyl)-2-oxoethyl]-2-methylpropionamide

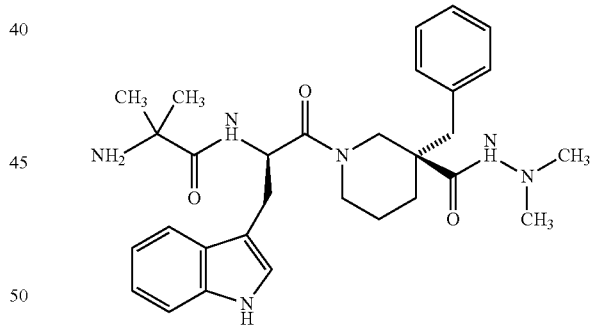

1-{(2R)-2-[N-((2E)-5-Amino-5-methylhex-2-enoyl)-N-methylamino]-3-(biphenyl-4-yl)propionyl}-4-benzylpiperidine-4-carboxylic acid ethyl ester

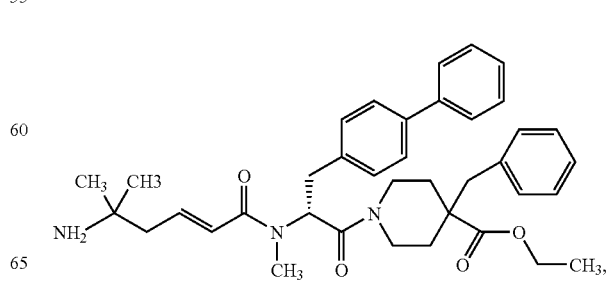

1-{(2R)-2-[N-((2E)-5-Amino-3,5-dimethylhex-2-enoyl)-N-methylamino]-3-(biphenyl-4-yl)propionyl}-4-benzylpiperidine-4-carboxylic acid ethyl ester

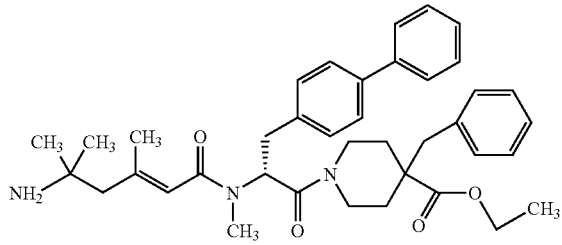

1-{(2R)-2-[N-((2E)-5-Amino-3,5-dimethylhex-2-enoyl)-N-methylamino]-3-(2-naphthyl)propionyl}-4-benzylpiperidine-4-carboxylic acid ethyl ester

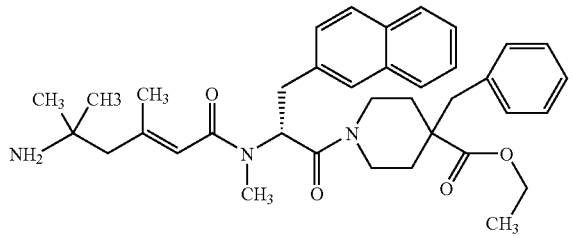

1-{(2R)-2-[N-((2E)-5-Amino-5-methylhex-2-enoyl)-N-methylamino]-3-(2-naphthyl)propionyl}-4-benzylpiperidine-4-carboxylic acid ethyl ester

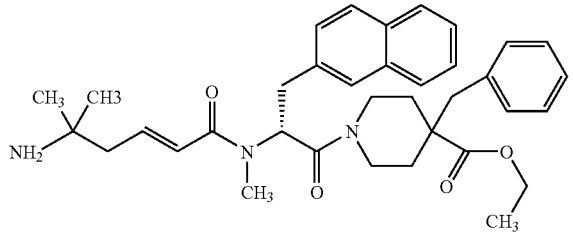

(3S)-1-[(2R)-2-((2E)-5-Amino-5-methylhex-2-enoylamino)-3-(1H-indol-3-yl) propionyl]-3-benzylpiperidine-3-carboxylic acid ethyl ester

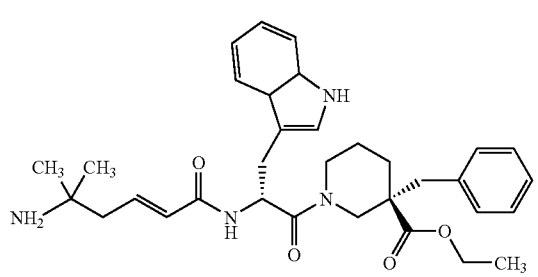

(3S)-1-[(2R)-2-((2E)-5-Amino-3,5-dimethylhex-2-enoylamino)-3-(1H-indol-3-yl) propionyl]-3-benzylpiperidine-3-carboxylic acid ethyl ester

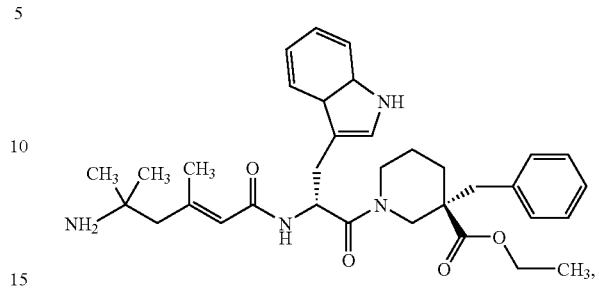

(3S)-1-[(2R)-2-(3-(Aminomethyl)benzoylamino)-3-(1H-indol-3-yl)propionyl]-3-benzylpiperidine-3-carboxylic acid ethyl ester

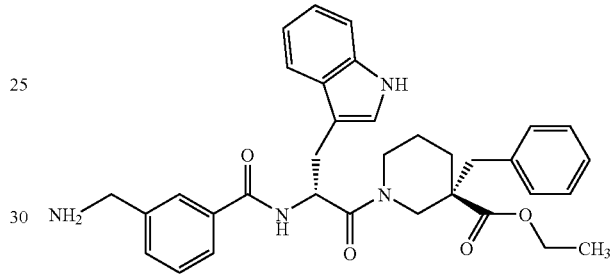

(2E)-5-Amino-5-methylhex-2-enoic acid N-{(1R)-2-[4-benzyl-4-(N',N'-dimethyl-hydrazinocarbonyl)piperidin-1-yl]-1-(2-naphthyl)methyl)-2-oxoethyl}-N-methylamide

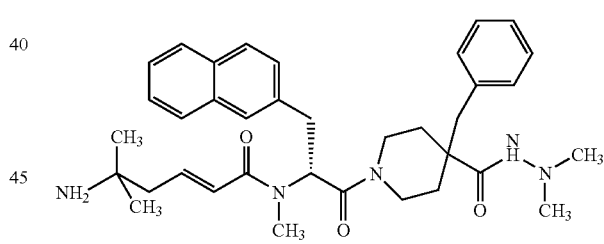

(2E)-5-Amino-5-methylhex-2-enoic acid N-[(1R)-2-[3-benzyl-3-(N',N'-dimethyl-hydrazinocarbonyl)-piperidin-1-yl]-1-((1H-indol-3-yl)methyl)-2-oxoethyl]amide

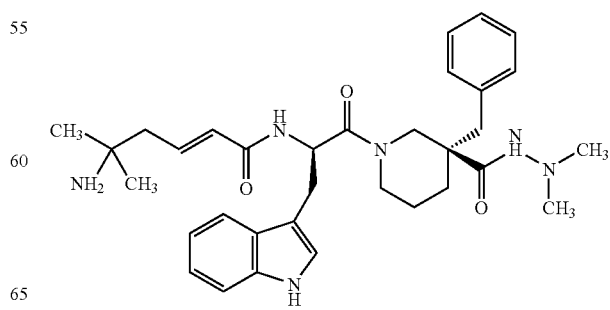

(2E)-5-Amino-5-methylhex-2-enoic acid N-{(1R)-2-[3-benzyl-3-(N',N'-dimethyl-hydrazinocarbonyl)-piperidin-1-yl]-1-((2-naphthyl)methyl)-2-oxoethyl}-N-methyl-amide

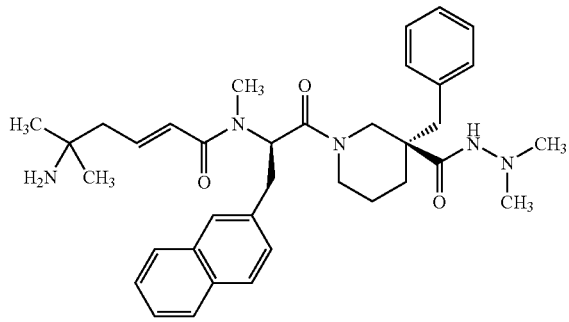

2E)-5-Amino-5-methylhex-2-enoic acid {(1R)-2-[3-benzyl-3-N',N-dimethyl-hydrazinocarbonyl)piperidin-1-yl]-1-(benzyloxymethyl)-2-oxoethyl}amide

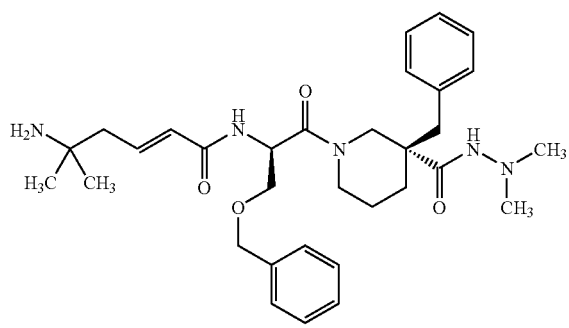

2-Amino-N-{2-[3-benzyl-3-(N,N'-dimethylhydrazinocarbonyl)piperidin-1-yl]-1-naphthyl)methyl)-2-oxo-ethyl}-2-methyl-propionamide

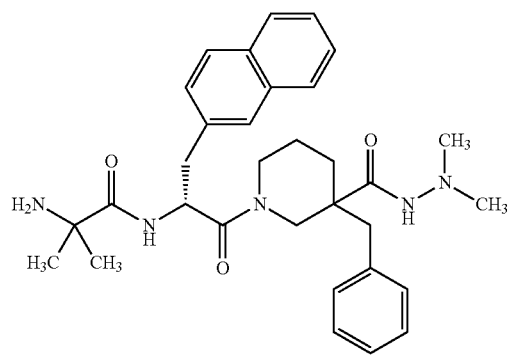

2-Amino-N-{(1R)-2-[3-benzyl-3-(N',N'-dimethylhydrazinocarbonyl)piperidin-1-yl]-1-((biphenyl-4-yl)methyl)-2-oxoethyl}-2-methylpropionamide 2-Amino-N-{(1R)-2-[3-benzyl-3-(N',N'-dimethylhydrazinocarbonyl)piperidin-1-yl]-1-((1H-indol-3-yl)methyl)-2-oxoethyl}-2-methylpropionamide

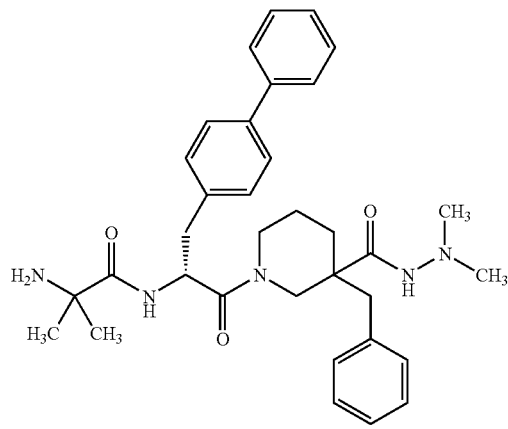

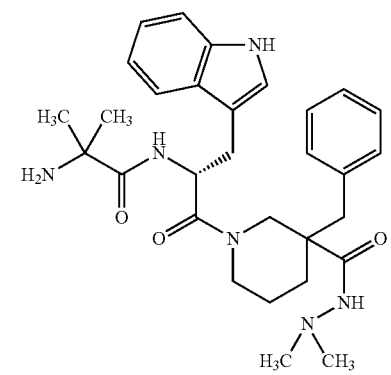

2-Amino-N-{2-[3-benzyl-3-(N'-dimethylhydrazinocarbonyl)piperidin-1-yl]-1-(benzyloxymethyl)-2-oxoethyl}-2-methylpropionamide

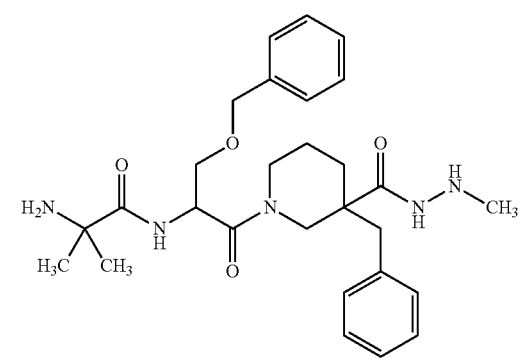

2-Amino-N-{2-[3-benzyl-3-(N,N-dimethylhydrazinocarbonyl)piperidin-1-yl]-1-(benzyloxymethyl)-2-oxoethyl}-2-methylpropionamide

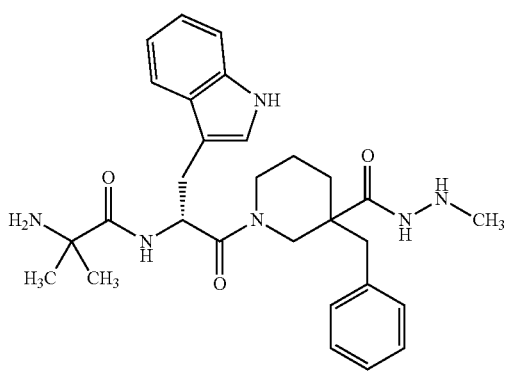

1-[(2R)-2-(2-Amino-2-methylpropionylamino)-3-(1-H-indol-3-yl)propionyl]-3-benzylpiperidine-3-carboxylic acid (pyrrolidin-1-yl)amide

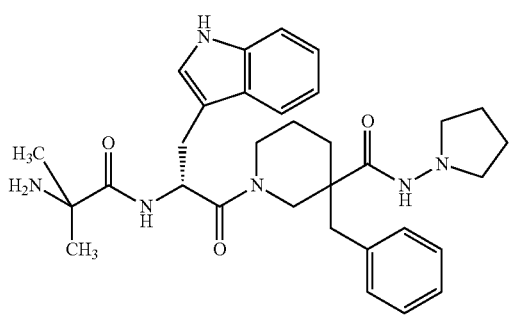

(2E)-5-Amino-5-Methylhex-2-enoic acid N-((1R)-1-{N-[(1R)-1-benzyl-2-(4-((dimethylamino)methyl)piperidin-1-yl)-2-oxoethyl]-N-methylcarbamoyl}-2-(2-naphthyl)ethyl)-N-methylamide

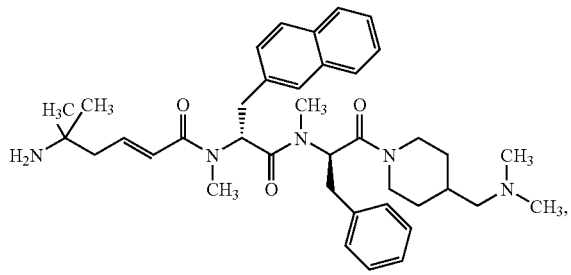

(2E)-5-Amino-5-Methylhex-2-enoic acid N-((1R)-1-{N-[(1R)-1-benzyl-2-((3S)-3-(dimethylaminomethyl)piperidin-1-yl)-2-oxoethyl]-N-methylcarbamoyl}-2-(2-naphthyl)ethyl)-N-methylamide

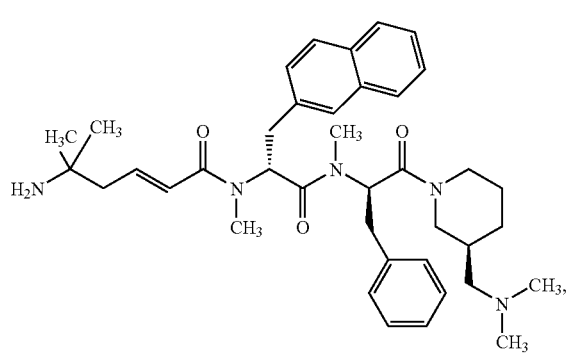

(2E)-4-(1-Aminocyclobutyl)but-2-enoic acid N-((1R)-1-{N-[(1R)-1-benzyl-2-((3S)-3-(dimethylaminomethyl)piperidin-1-yl)-2-oxoethyl]-N-methylcarbamoyl}-2-(2-naphthyl)ethyl)-N-methylamide

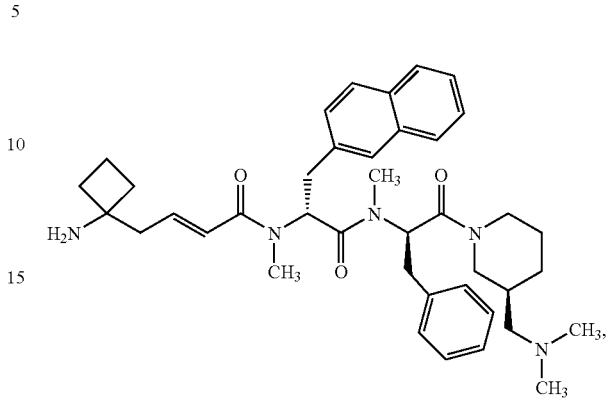

(2E)-5-Amino-5-methylhex-2-enoic acid N-((1R)-1-{N-[(1R)-1-benzyl-2-((2S)-2-((dimethylamino)methyl)pyrrolidin-1-yl)-2-oxoethyl]-N-methylcarbamoyl}-2-(2-naphthyl)ethyl)-N-methylamide

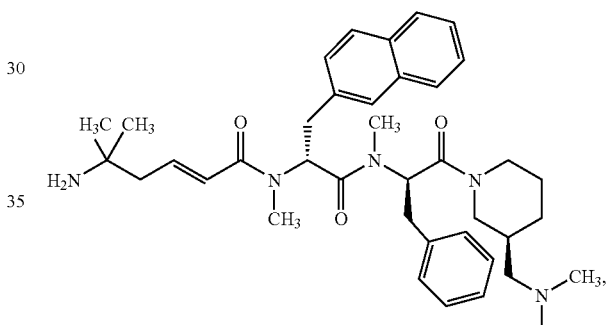

N-((1R)-1-{N-[(1R)-1-Benzyl-2-((2S)-2-((dimethylamino)methyl)pyrrolidin-1-yl)-2-oxoethyl]-N-methylcarbamoyl}-2-(2-naphthyl)ethyl)-N-methyl-3-((methylamino)methyl)benzamide

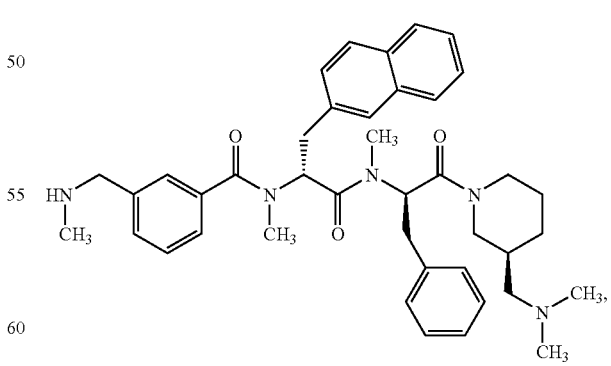

(2E)-5-Amino-5'-methylhex-2enoic acid N-((1R-1-{N-[(1R)-1-benzyl-2-(4-(dimethylamino)piperidin-1-yl)-2=oxoethyl]-N-methylcarbamoyl}-2-(2-naphthyl)ethyl)-N-methylamide.

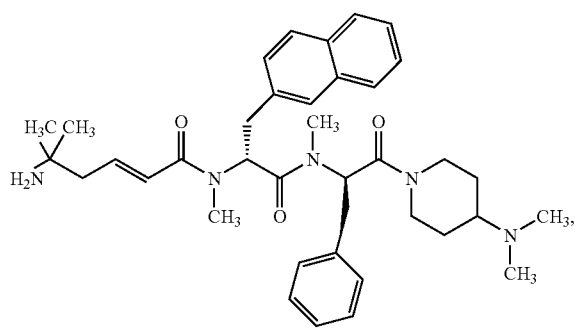

(2E)-5-Amino-5-methylhex-2-enoic acid N-methyl-N-[(1R)-1-(N-methyl-N-{(1R)-1-[N-methyl-N-(1-methylpiperidin-4-yl) carbamoyl]-2-phenylethyl}carbamoyl)-2-(2-naphthyl)ethyl]amide

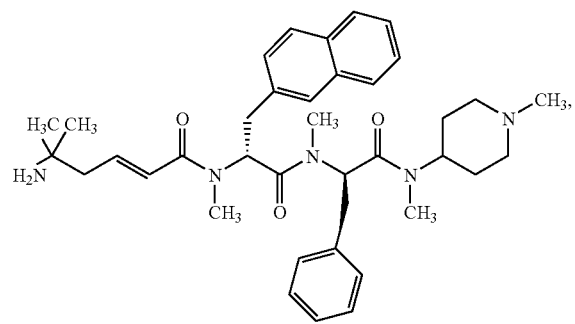

3-Aminomethyl-N-((1R)-1-{N-[(1R)-1-benzyl-2-(4-methylpiperazin-1-yl)-2-oxoethyl]-methylcarbamoyl}-2-(2-naphthyl)ethyl)-N-methylbenzamide

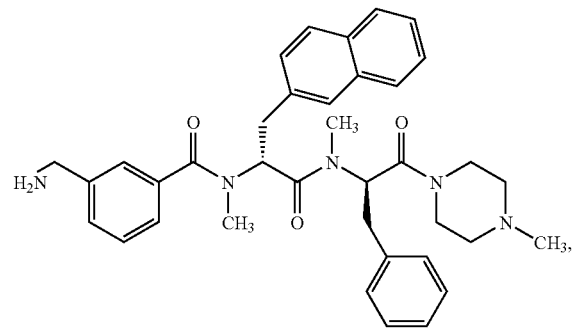

(2E)-5-Amino-5-methylhex-2-enoic acid N-((1R)-1-{N-[(1R)-1-benzyl-2-(4-methylpiperazin-1-yl)-2-oxoethyl]-N-methylcarbamoyl}-2-(2-naphthyl)-N-methylamide

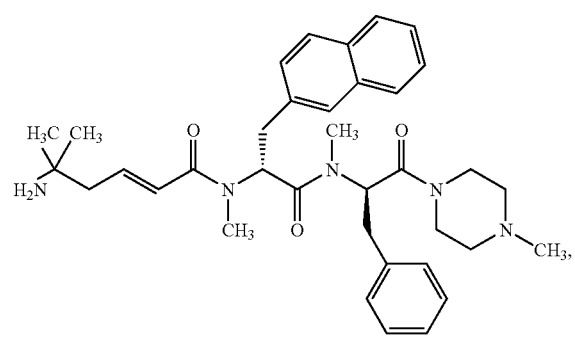

(2E)-5-Amino-5-methylhex-2-enoic acid N-methyl-N-((1R)-1-{N-methyl-N-[(1R)-2-phenyl-1-((2,6,6-tetramethylpiperidin-4-yl)carbamoyl)ethyl]carbamoyl}-2-(2-naphthyl)ethyl)amide

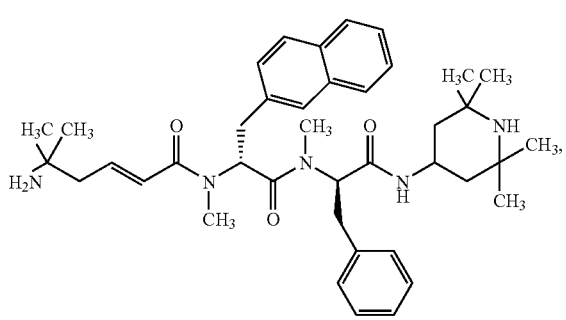

3-Aminomethyl-N-methyl-N-((1R) 1-{N-methyl-N-[(1R)-2-phenyl-1-((2,2,6,6-tetramethylpiperidin-4-yl) carbamoyl)ethyl]carbamoyl}-2-(2-naphthyl)ethyl)benzamide

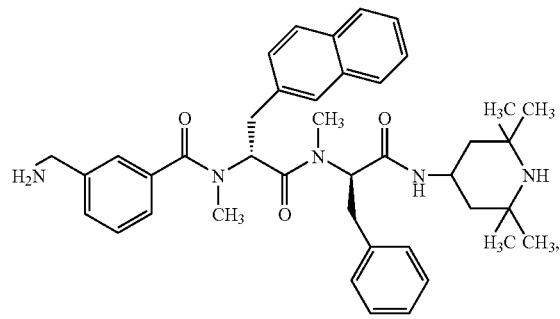

(2E)-5-Amino-3,5-dim ethylhex-2-enoic acid N-methyl-N-((1R-1-{N-methyl-N-[(1R)-2-phenyl-1-((2,2,6,6-tetramethylpiperidin-4-yl) carbamoyl)ethyl]carbamoyl}-2-(2-naphthyl)ethyl)amide

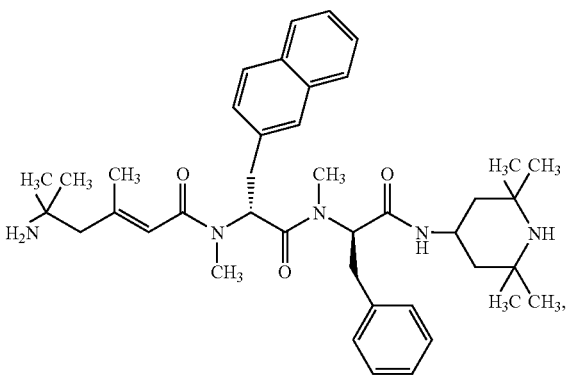

(2E)-4-(1-Aminocyclobutyl)but-2-enoic acid N-((1R)1-{N-[(1R)1-benzyl-2-(4-methylpiperazin-1-yl)-2-oxoethyl]-N-methylcarbamoyl}-2-(2-naphthyl)ethyl)-N-methylamide

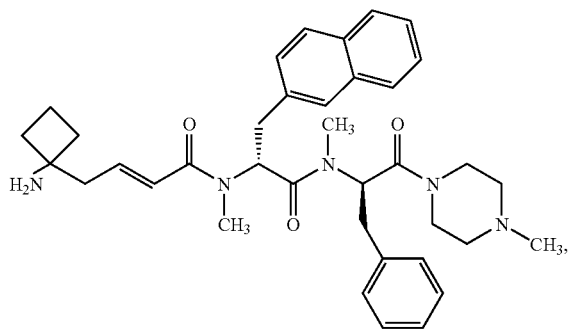

(2E)-5-Amino-3,5-dimethylhex-2-enoic acid N-((1R)1-{N-[(1R)1-benzyl-2-(4-methylpiperazin-1-yl)-2-oxoethyl]-N-methylcarbamoyl}-2-(2-naphthypethyl)-N-methylamide

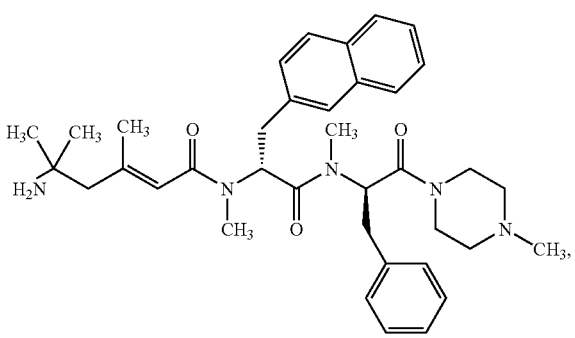

(2E)-4-(1-Aminocyclobutyl)but-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

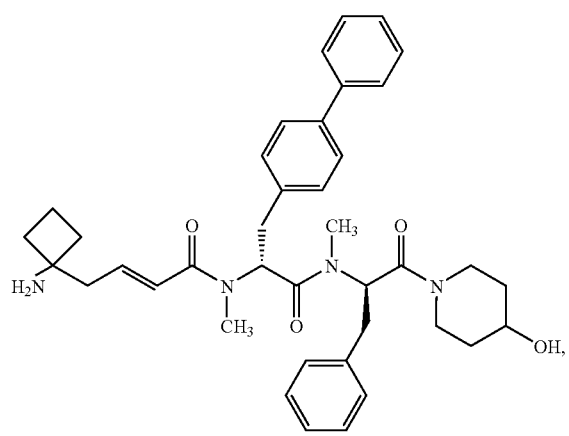

(2E)-5-Amino-3,5-dimethylhex-2enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

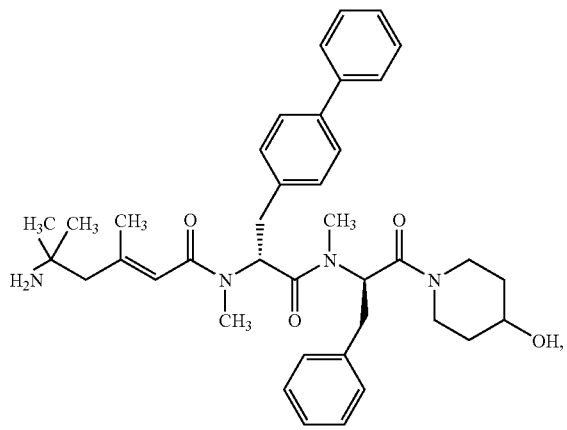

(2E)-5-Amino-5-methylhex-2-enoic acid N-((1R)-1-{N-[(1R)-1-benzyl-2-(4-hydroxypiperidin-1-yl)-2-oxoethyl]-N-methylcarbamoyl}-2-(2-naphthyl)ethyl)-N-methylamide

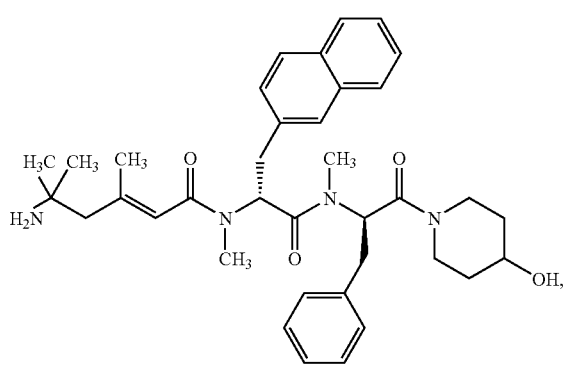

(2E)-5-Amino-3,5-dimethylhex-2-enoic acid N-((1R)-1-{N-[(1R)-1-benzyl-2-(4-hydroxypiperidin-1-yl)-2-oxoethyl]-N-methylcarbamoyl}-2-(2-naphthyl)ethyl)-N-methylamide

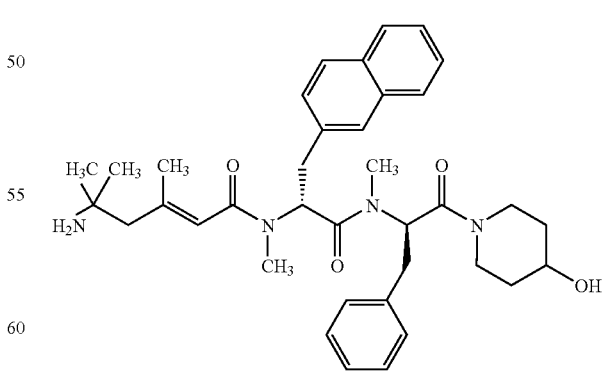

(2E)-4-(1-Amino cyclobutyl)but-2-enoic acid N-((1R)-1-{N-[(1R)-1-benzyl-2-(4-hydroxypiperidin-1-yl)-2-oxoethyl]-N-methylcarbamoyl}-2-(2-naphthyl)ethyl)-N-methylamide

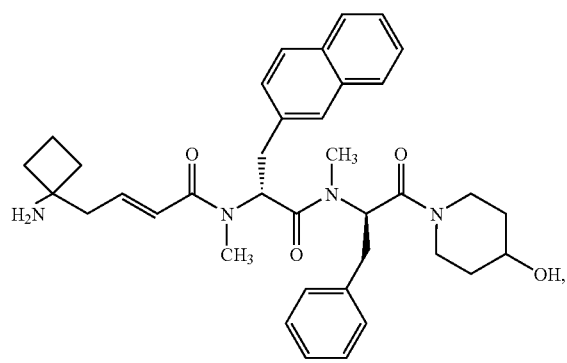

(2E)-5-Amino-5-methylhex-2-enoic acid N-((1R)-1-{N-[(1R)-1-(4-fluorobenzyl)-2-(4-hydroxypiperidin-1-yl)-2-oxoethyl]-N-methylcarbamoyl}-2-(2-naphthyl)ethyl)-N-methylamide

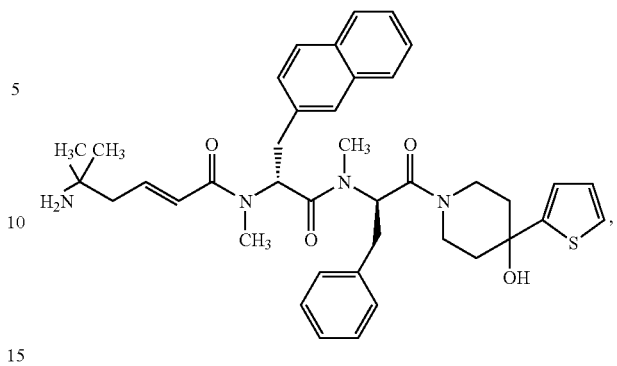

(2E)-5-Amino-5-methylhex-2-enoic acid N-((1R)-1-{N-[(1R)-1-(3-hydroxycyclohexylcarbamoyl)-2-phenylethyl]-N-methylcarbamoyl}-2-(2-naphthyl)ethyl)-N-methylamide

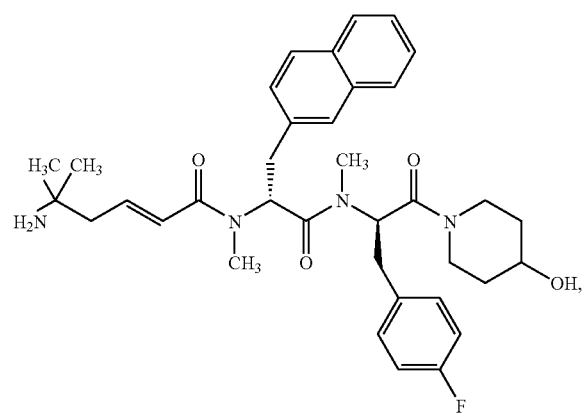

(2E)-5-Amino-3,5-dimethylhex-2-enoic acid N-((1R)-1-{N-[(1R)-1-(4-fluorobenzyl)-2-(4-hydroxypiperidin-1-yl)-2-oxoethyl)-N-methylcarbamoyl}-2-(2-naphthyl)ethyl)-N-methylamide

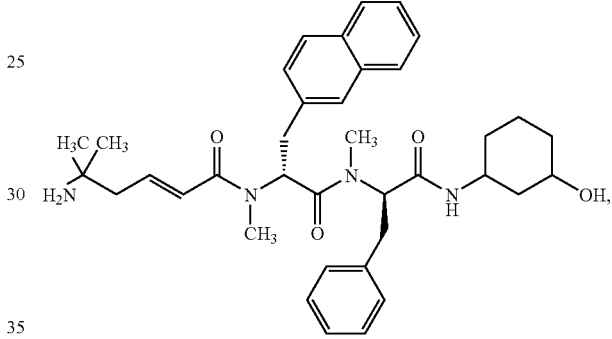

(2E)-4-(1-Aminocyclobutyl)but-2-enoic acid N-((1R)-1-[(1R)-1-benzyl-2-(4-(dimethylamino)piperidin-1-yl)-2-oxoethyl]-N-methylcarbamoyl-2-(2-naphthypethyl)-N-methylamide

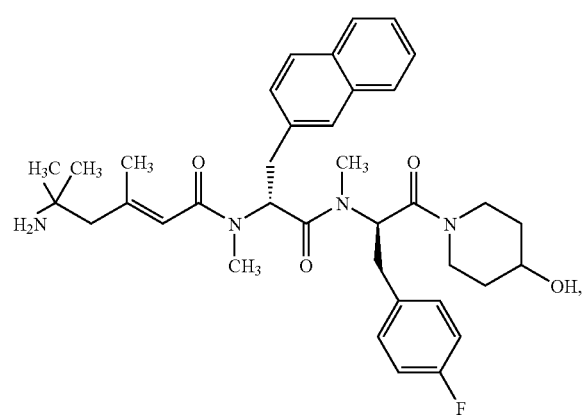

(2E)-5-Amino-5-methylhex-2-enoic acid N-((1R)-1-{N-[(1R)-1-benzyl-2-(4-hydroxy-4-(2-thienyl)piperidin-1-yl)-2-oxoethyl]-N-methylcarbamoyl}-2-(2-naphthyl)ethyl)-N-methylamide

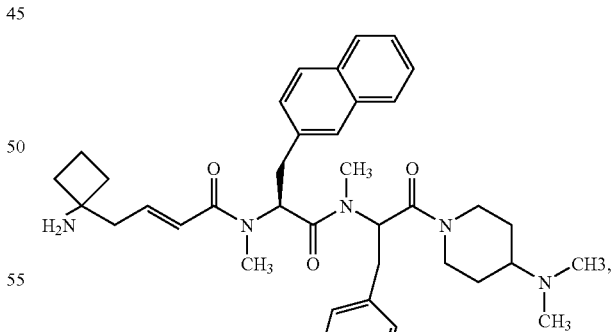

(2E)-5-Amino-5-methylhex-2-enoic acid N-((1R)-1-{N-[(2R)-2-(4-hydroxypiperidin-1-yl)-2-oxo-1-((2-thienyl)methyl)ethyl]-N-methylcarbamoyl}-2-(2-naphthyl)ethyl)-N-methylamide

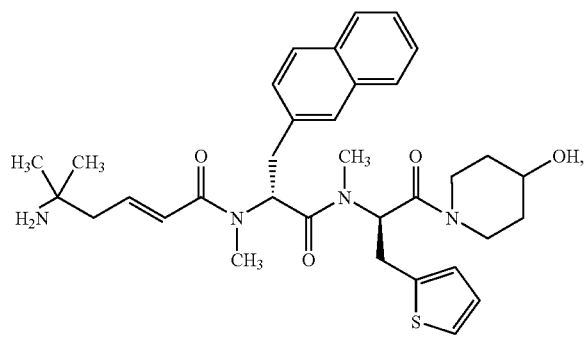

(2E)-5-Amino-3,5-dimethylhex-2-enoic acid N-((1R)-1-{N-[(2R)-2-(4-hydroxypiperidin-1-yl)-2-oxo-1-((2-thienyl)methyl)ethyl]-N-methylcarbamoyl}-2-(2-naphthyl)ethyl)-N-methylamide

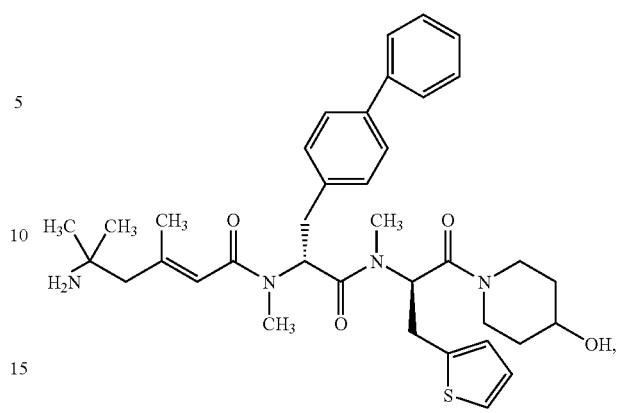

(2E)-5-M ethyl-5-(methylamino)hex-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

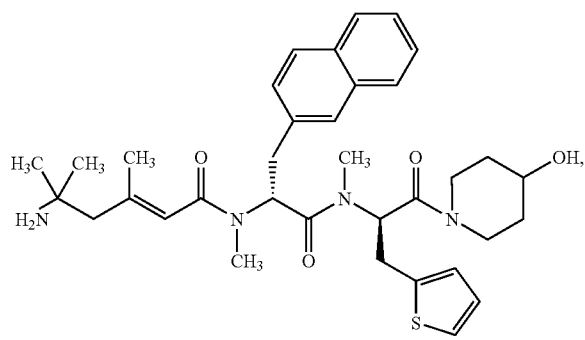

(2E)-5-Amino-5-methylhex-2-enoic acid N-((1R)-2-(biphenyl-4-yl)-1-{N-[(2R)-2-(4-hydroxypiperidin-1-yl)-2-oxo-1-((2-thienyl)methyl)ethyl]-N-methylcarbamoyl}ethyl)-N-methylamide

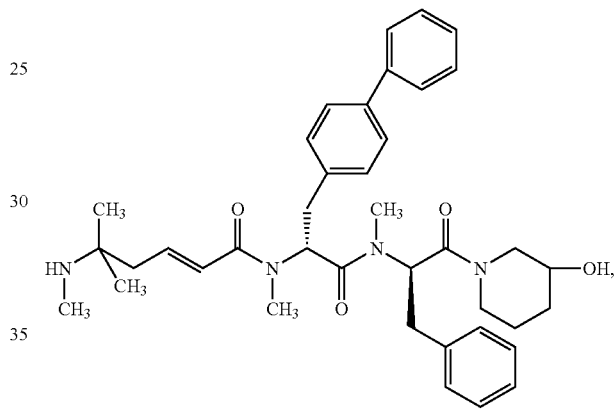

(2E)-4-(1-Aminocyclobutyl)but-2-enoic acid ((1R)-1-{N-[(1R)-1-benzyl-2-(4-hydroxypiperidin-1-yl)-2-oxoethyl]-N-methylcarbamoyl}-2-(biphenyl-4-yl)ethyl)amide

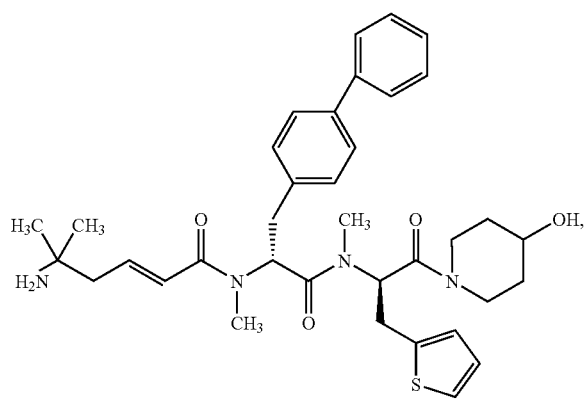

(2E)-5-Amino-3,5-dimethylhex-2-enoic acid N-((1R)-2-(biphenyl-4-yl)-1-{N-[(1R)-2-(4-hydroxypiperidin-1-yl)-2-oxo-1-((2-thienyl)methyl)ethyl]-N-methylcarbamoyl}ethyl)-N-methylamide and pharmaceutically acceptable salts thereof.

In another embodiment, the growth hormone secretagogue is represented by structural Formula VI or a pharmaceutically acceptable salt, solvate or hydrate thereof. The chemical name for the compound represented by structural Formula VI is: (2E)-4-(1-aminocyclobutyl)but-2-enoic acid N-((1R)-1-{N-[(1R)-1-benzyl-2-(4-hydroxypiperidin-1-yl)-2-oxoethyl]-N-methylcarbomoyl}-2-(biphenyl-4-yl)ethyl)-N-methylamide.

VI

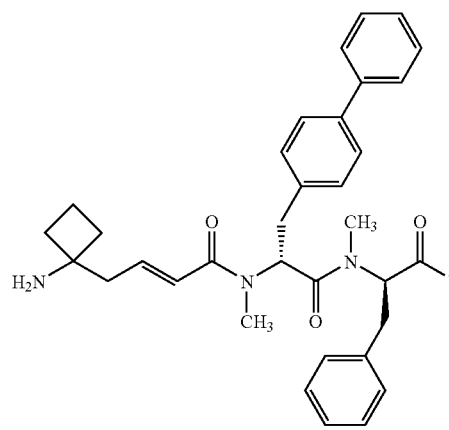

In yet another embodiment, the growth hormone secretagogue is represented by structural Formula VII or a pharmaceutically acceptable salt, solvate or hydrate thereof. The chemical name of the compound represented by structural Formula VII is: (2E)-5-amino-5-methylhex-2-enoic acid N-methyl-N-((1R)-1-{N-methyl-N-[(1R)-2-phenyl-1-(N,N',N'-trimethylhydrazino carbonyl)ethyl]carbamoyl}-2-(2-naphthyl)ethyl)amide.

VII

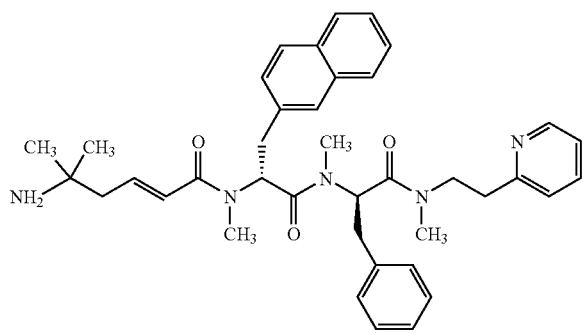

In one embodiment, the growth hormone secretagogue is represented by structural Formula VIII or a pharmaceutically acceptable salt, solvate or hydrate thereof.

The chemical name of the compound represented by structural Formula VIII is: (2E)-5-amino-5-methylhex-2-enoic acid N-methyl-N-((1R)-1-{N-methyl-N-[(1R)-2-phenyl-1-(N,N',N'-trimethylhydrazinocarbonyl)ethyl]carbamoyl}2-(2-naphthyl)ethyl)amide.

VIII

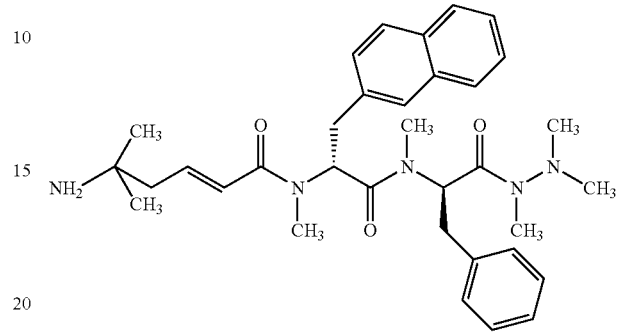

In another embodiment, the growth hormone secretagogue is represented by structural Formula IX or a pharmaceutically acceptable salt, solvate or hydrate thereof. The chemical name for the compound represented by structural Formula IX is: 2-amino-N-(2-(2-(N-((2R)-2-(N-((2E)-5-amino-5-methylhex-2-enoyl)-N-methylamino)-3-(2-napthyl)propionyl)-N-methylamino)ethyl)phenylacetamide.

IX

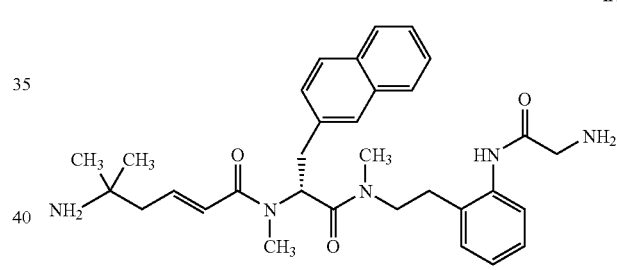

In further embodiments, the growth hormone secretagogue can be selected from GHRP-1 (Formula X), GHRP-2 (Formula XI), GHRP-6 (Formula XII), NN703 (Formula XIII), Ipamorelin (Formula XIV), Capromorelin (Formula XV) and MK-677 (Formula XVI) and analogs of any of the above.

X

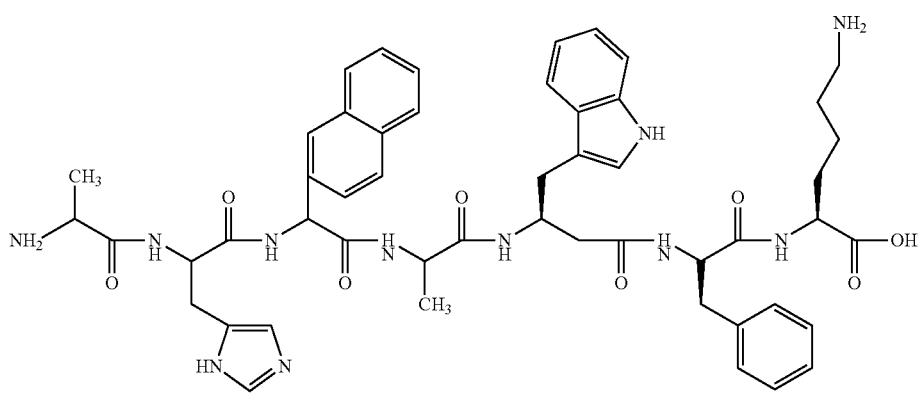

XI

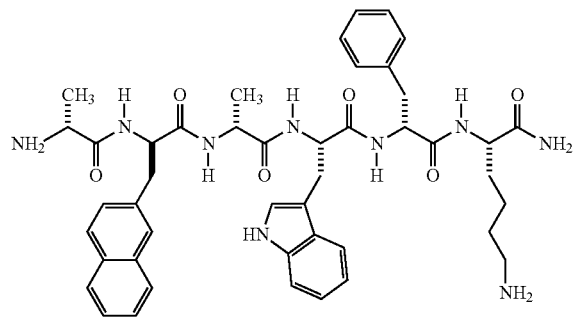

XII

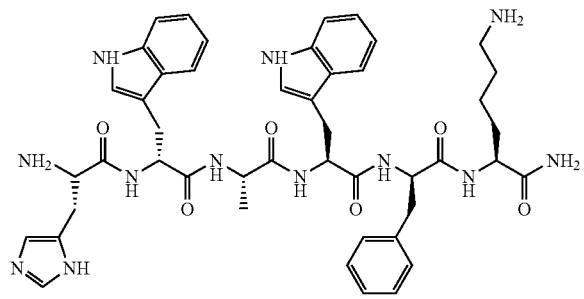

XIII

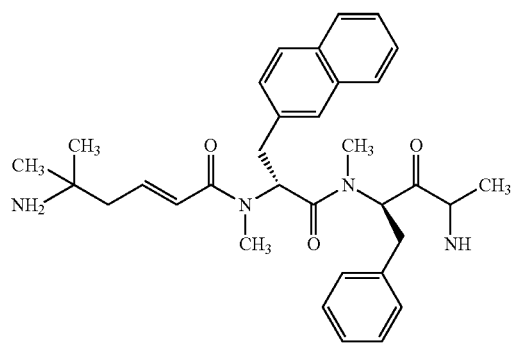

XIV

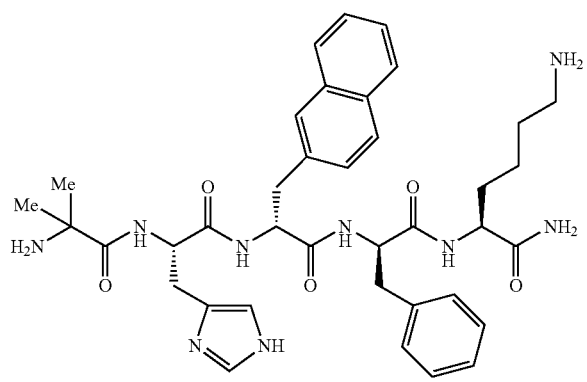

XV

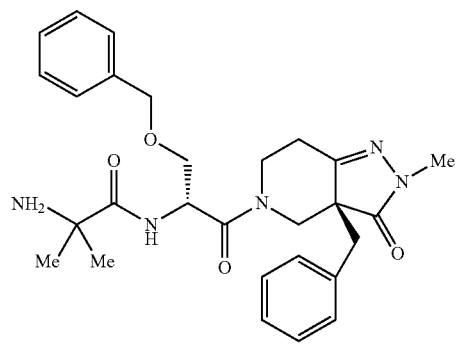

XVI

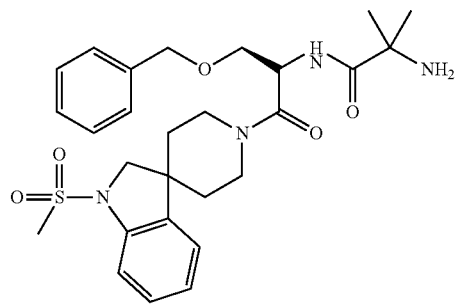

Peripherally Acting Opioid Antagonists

Peripherally acting opioid receptor antagonists, such as methylnaltrexone, naloxone, naltrexone, nalmefene and alvimopan (ENTEREG™), which do not cross the blood-brain barrier, can be administered to treat opioid induced side effects without provoking opioid withdrawal symptoms or reverse analgesia. (Holzer P., "Opioids and Opioid Receptors in the Enteric Nervous System: From a Problem in Opioid Analgesia to a Possible New Prokinetic Therapy in Humans," *Neurosci Lett.*, 361(1-3):192-5 (2004), incorporated herein by reference).

As used herein, peripherally acting opioid antagonists refer to opioid antagonists that act peripherally (i.e., not centrally, for example, do not act on the central nervous system).

Proton Pump Inhibitors

Proton pump inhibitors suppress gastric acid secretion, the final step of acid production, by specific inhibition of the $H^+$ $K^+$-ATPase enzyme system at the secretory surface of gastric parietal cells. Proton pump inhibitors include benzimidazole compounds, for example, esomeprazole (NEXIUM®), omeprazole (PRILOSEC™), lansoprazole (PREVACID™), and pantoprazole. These proton pump inhibitors contain a sulfinyl group situated between substituted benzimidazole and pyridine rings. At neutral pH, esomeprazole, omeprazole, lansoprazole, and pantoprazole are chemically stable, lipid soluble, weak bases that are devoid of inhibitory activity. These uncharged weak bases reach parietal cells from the blood and diffuse into the secretory canaliculi, where the drugs become protonated and thereby trapped. The protonated species rearranges to form a sulfenic acid and a sulfenamide, the latter species capable of interacting with sulfhydryl groups of $H^+K^+$-ATPase. Full inhibition occurs with two molecules of inhibitor per molecule of enzyme. The specificity of the effects of proton pump inhibitors is believed to derive from: a) the selective distribution of $H^+K^+$-ATPase; b) the requirement for acidic conditions to catalyze generation of the reactive inhibitor; and c) the trapping of the protonated drug and the cationic sulfenamide within the acidic canaliculi and adjacent to the target enzyme. Goodman & Gilman's The Pharmacological Basis of Therapeutics, 9th Edition, pp. 901-915 (1996), incorporated herein by reference.

H₂ Antagonists

H₂ receptor antagonists competitively inhibit the interaction of histamine with H₂ receptors. They are highly selective and have little or no effect on H₁ receptors. Although H₂ receptors are present in numerous tissues, including vascular and bronchial smooth muscle, H₂ receptor antagonists interfere remarkably little with physiological functions other than gastric acid secretion. H₂ receptor antagonists include, but are not limited to, nizatidine (AXID™), ranitidine (ZANTAC™ and TRITEC™), famotidine (PEPCID AC™), and cimetidine (TAGAMET™) and rabeprazole (ACIPHEX™). Goodman & Gilman's The Pharmacological Basis of Therapeutics, 9th Edition, pp. 901-915 (1996), incorporated herein by reference.

H₂ receptor antagonists inhibit gastric acid secretion elicited by histamine, other H₂ agonists, gastrin, and, to a lesser extent, muscarinic agonists. H₂ receptor antagonists also inhibit basal and nocturnal acid secretion.

Antacids

Compounds of the invention can be administered with antacids to neutralize gastric acid. For example, aluminum and magnesium hydroxide (MAALOX™ and MYLANTA™) neutralize gastric acidity, resulting in increase in pH in the stomach and duodenal bulb.

Laxatives

Laxatives come in various forms: liquids, tablets, suppositories, powders, granules, capsules, chewing gum, chocolate-flavored wafers, and caramels. The basic types of laxatives are bulk-forming laxatives, lubricant laxatives, stool softeners (also called emollient laxatives), and stimulant laxatives.

Bulk-Forming Laxatives

Bulk-forming laxatives contain materials, such as cellulose and psyllium, that pass through the digestive tract without being digested. In the intestines, these materials absorb liquid and swell, making the stool soft, bulky, and easier to pass. The bulky stool then stimulates the bowel to move. Laxatives in this group include such brands as FIBERCON®, FIBER-ALL®, and METAMUCIL®.

Lubricant Laxatives

Mineral oil is the mostly widely used lubricant laxative. Taken by mouth, the oil coats the stool. This keeps the stool moist and soft and makes it easier to pass. Lubricant laxatives are often used for patients who need to avoid straining (e.g., after abdominal surgery).

Stool softeners (Emollient Laxatives)

As their name suggests, stool softeners make stools softer and easier to pass by increasing their moisture content. This type of laxative does not really stimulate bowel movements, but it makes it possible to have bowel movements without straining. Stool softeners are best used to prevent constipation in people who need to avoid straining, because of recent surgery, for example. Three stool-softening agents are available: docusate sodium (COLACE®, REGUTOL®, and others), docusate calcium (SURFAK®, DC SOFTGELS®) and docusate potassium (DIALOSE®, DIOCTO-K®).

Serotonin 5-HT₄ Agonist

The 5-HT₄ agonists speed up movement of bowel contents through the colon and reduces sensitivity to intestinal nerve stimulation. Suitable serotonin 5-HT₄ agonists which can be used in combination with the compounds of the invention include sumatriptan, rauwolscine, yohimbine, metoclopramide, prucalopride and tegaserod (ZELNORM®). Spiller R., "Serotonergic Modulating Drugs for Functional Gastrointestinal Diseases," *Br J Clin Pharmacol.* 54:11-20 (2002) and U.S. Pat. No. 6,413,988, incorporated herein by reference.

Motilin Receptor Agonists

Motilin is a peptide of 22 amino acids which is produced in the gastrointestinal system of a number of species. Motilin induces smooth muscle contractions in the stomach tissue of dogs, rabbits, and humans as well as in the colon of rabbits. Apart from local gastrointestinal intestinal tissues, motilin and its receptors have been found in other tissues.

Aside from motilin itself, there are other substances which are agonists of the motilin receptor and which elicit gastrointestinal emptying. One of those agents is the antibiotic erythromycin. Studies have shown that erythromycin elicits biological responses that are comparable to motilin itself and therefore can be useful in the treatment of diseases such as chronic idiopathic intestinal pseudo-obstruction and gastroparesis. Weber, F. et al., *The American Journal of Gastroenterology,* 88:4, 485-90 (1993), incorporated herein by reference.

Dopamine Antagonists

Dopamine antagonists are drugs that bind to, but do not activate, dopamine receptors thereby blocking the actions of dopamine or exogenous agonists. This class of drugs includes, but are not limited to, bethanecol, metoclopramide, domperidone, amisulpride, clebopride, mosapramine, nemonapride, remoxipride, risperidone, sulpiride, sultopride and ziprasidone.

Cholinesterase Inhibitors

The term "cholinesterase inhibitor" refers to one or more agents that prolong the action of acetylcholine by inhibiting its destruction or hydrolysis by cholinesterase. Cholinesterase inhibitors are also known as acetylcholinesterase inhibitors. Examples of cholinesterase inhibitors include, but are not limited to, edrophonium, neostigmine, neostigmine methylsulfate, pyridostigmine, tacrine and physostigmine, ambenonium chloride (MYTELASE®), edrophonium chloride (TENSILON®), neostigmine (PROSTIGMINE®), piridogstimina (MESTINON®), distigmine bromide, eptastigmine, galanthamine, axeclidine, acetylcholine bromine, acetylcholine chloride, aclatonium napadisilate, benzpyrinium bromide, carbachol, carponium chloride, cemecarium bromide, dexpanthenol, diisopropyl paraoxon, echothiophate chloride, eseridine, furtrethonium, methacholine chloride, muscarine, oxapropanium idoide, and xanomeline.

Subject, as used herein, refers to animals such as mammals, including, but not limited to, primates (e.g., humans), cows, sheep, goats, horses, pigs, dogs, cats, rabbits, guinea pigs, rats, mice or other bovine, ovine, equine, canine, feline, rodent or murine species. In a preferred embodiment, the mammal is a human.

As used herein, treating and treatment refer to stimulating (e.g., inducing) motility of the gastrointestinal system.

As used herein, therapeutically effective amount refers to an amount sufficient to elicit the desired biological response. In the present invention, the desired biological response is stimulating (e.g., inducing) motility of the gastrointestinal system. In one embodiment, the desired biological response is stimulating (e.g., inducing) motility of the gastrointestinal system to treat opioid induced constipation in a subject in need thereof. In another embodiment, the subject is using opioids for post-surgical pain management. In yet another embodiment, the subject is using opioids for chronic pain management.

In one embodiment, the desired biological response is stimulating (e.g., inducing) motility of the gastrointestinal system to treat diabetes related gastroparesis in a subject in need thereof.

In another embodiment, the desired biological response is stimulating (e.g., inducing) motility of the gastrointestinal system to treat gastroesophageal reflux disease in a subject in need thereof. In yet another embodiment, the gastroesophageal reflux disease is nocturnal gastroesophageal reflux disease.

In one embodiment, the desired biological response is stimulating (e.g., inducing) motility of the gastrointestinal system to treat irritable bowel syndrome in a subject in need thereof. In another embodiment the irritable bowel syndrome is constipation-predominant irritable bowel syndrome. In yet another embodiment, the irritable bowel syndrome is constipation/diarrhea irritable bowel syndrome.

In another embodiment, the desired biological response is stimulating (e.g., inducing) motility of the gastrointestinal system to treat constipation in a subject in need thereof.

In another embodiment, the desired biological response is stimulating (e.g., inducing) motility of the gastrointestinal system to treat post-operative ileus in a subject in need thereof.

The therapeutically effective amount or dose will depend on the age, sex and weight of the patient, and the current medical condition of the patient. The skilled artisan will be able to determine appropriate dosages depending on these and other factors to achieve the desired biological response.

A suitable dose per day for the growth hormone secretagogue can be in the range of from about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 µg to about 3,500 mg, about 5 µg to about 3,000 mg, about 10 µg to about 2,600 mg, about 20 µg to about 2,575 mg, about 30 µg to about 2,550 mg, about 40 µg to about 2,500 mg, about 50 µg to about 2,475 mg, about 100 µg to about 2,450 mg, about 200 µg to about 2,425 mg, about 300 µg to about 2,000, about 400 µg to about 1,175 mg, about 500 µg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg.

Other suitable doses per day for the growth hormone secretagogue include doses of about or greater than 1 ng, about 5 ng, about 10 ng, about 20 ng, about 30 ng, about 40 ng, about 50 ng, about 100 ng, about 200 ng, about 300 ng, about 400 ng, about 500 ng, about 1 µg, about 5 µg, about 10 µg, about 20 µg, about 30 µg, about 40 µg, about 50 µm, about 100 µg, about 200 µg, about 300 µg, about 400 µg, about 500 µg (0.5 mg), about 1 mg, about 1.25 mg, about 1.5 mg, about 2.0 mg, about 2.5 mg, about 3.0 mg, about 3.5 mg, about 4.0 mg, about 4.5 mg, about 5 mg, about 10 mg, about 20 mg, about 30 mg, about 40 mg, about 50 mg, about 100 mg, about 200 mg, about 300 mg, about 400 mg, about 500 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1125 mg, about 1150 mg, about 1175 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, about 2500 mg, about 2525 mg, about 2550 mg, about 2575 mg, about 2600 mg, about 3,000 mg, about 3,500 mg, about 4,000 mg, about 4,500 mg, about 5,000 mg, about 5,500 mg, about 6,000 mg, about 6,500 mg, about 7,000 mg, about 7,500 mg, about 8,000 mg, about 8,500 mg, about 9,000 mg, or about 9,500 mg.

In a particular embodiment, a suitable dose of the growth hormone secretagogue can be in the range of from about 0.20 mg to about 4000 mg per day, such as from about 1 mg to about 4000 mg, for example, from about 5 mg to about 3000 mg, such as about 10 mg to about 2400 mg per day. The dose can be administered in a single dosage or in multiple dosages, for example from 1 to 4 or more times per day. When multiple dosages are used, the amount of each dosage can be the same or different.

A suitable dose for the additional therapeutic agent can be in same range as described above for the growth hormone secretagogue. The dose of growth hormone secretagogue and additional agent can be the same or different. Suitable doses for the additional agents can be found in the literature.

Combination Administration

Administration of a growth hormone secretagogue can take place prior to, after or at the same time as treatment with an additional therapeutic agent, such as, for example, a laxative, a $H_2$ receptor antagonist, a serotonin 5-$HT_4$ agonist, an antacid, an opioid antagonist, a proton pump inhibitor, or a combination thereof. The therapeutic agent can be administered during the period of growth hormone secretagogue administration but does not need to occur over the entire growth hormone secretagogue treatment period.

Modes of Administration

The compounds for use in the method of the invention can be formulated for administration by any suitable route, such as for oral or parenteral, for example, transdermal, transmucosal (e.g., sublingual, lingual, (trans)buccal), vaginal (e.g., trans- and perivaginally), (intra)nasal and (trans)rectal), subcutaneous, intramuscular, intradermal, intra-arterial, intravenous, inhalation, and topical administration.

Suitable compositions and dosage forms include tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays, dry powders or aerosolized formulations.

It is preferred that the compounds are orally administered. Suitable oral dosage forms include, for example, tablets, capsules or caplets prepared by conventional means with pharmaceutically acceptable excipients such as binding agents (e.g., polyvinylpyrrolidone or hydroxypropylmethylcellulose); fillers (e.g., lactose, microcrystalline cellulose or calcium phosphate); lubricants (e.g., magnesium stearate, talc or silica); disintegrates (e.g., sodium starch glycollate); or wetting agents (e.g., sodium lauryl sulphate). If desired, the tablets can be coated, e.g., to provide for ease of swallowing or to provide a delayed release of active, using suitable methods. Liquid preparation for oral administration can be in the form of solutions, syrups or suspensions. Liquid preparations (e.g., solutions, suspensions and syrups) are also suitable for oral administration and can be prepared by conventional means with pharmaceutically acceptable additives such as suspending agents (e.g., sorbitol syrup, methylcellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

As used herein, the term pharmaceutically acceptable salt refers to a salt of a compound to be administered prepared from pharmaceutically acceptable non-toxic acids including inorganic acids, organic acids, solvates, hydrates, or clathrates thereof. Examples of such inorganic acids are hydrochloric, hydrobromic, hydroiodic, nitric, sulfuric, and phosphoric. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like.

The growth hormone secretagogues disclosed can be prepared in the form of their hydrates, such as hemihydrate, monohydrate, dihydrate, trihydrate, tetrahydrate and the like and as solvates.

It is understood that growth hormone secretagogue compounds can be identified, for example, by screening libraries or collections of molecules using suitable methods. Another source for the compounds of interest are combinatorial libraries which can comprise many structurally distinct molecular species. Combinatorial libraries can be used to identify lead compounds or to optimize a previously identified lead. Such libraries can be manufactured by well-known methods of combinatorial chemistry and screened by suitable methods.

Stereochemistry

Many of the compounds described herein can have one or more chiral centers and therefore can exist in different enantiomeric forms. If desired, a chiral carbon can be designated with an asterisk (*). When bonds to the chiral carbon are depicted as straight lines in the formulas of the invention, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When a compound of the present invention has two or more chiral carbons, it can have more than two optical isomers and can exist in diastereoisomeric forms. For example, when there are two chiral carbons, the compound can have up to 4 optical isomers and 2 pairs of enantiomers ((S,S)/(R,R) and (R,S)/(S,R)). The pairs of enantiomers (e.g., (S,S)/(R,R)) are mirror image stereoisomers of one another. The stereoisomers which are not mirror-images (e.g., (S,S) and (R,S)) are diastereomers. The diastereoisomeric pairs may be separated by methods known to those skilled in the art, for example chromatography or crystallization and the individual enantiomers within each pair may be separated as described above. The present invention includes each diastereoisomer of such compounds and mixtures thereof.

Variable Definitions

In the above structural formulas and throughout the present specification, the following terms have the indicated meanings:

The $C_{1-6}$-alkyl, $C_{1-6}$-alkylene, $C_{1-4}$-alkyl or $C_{1-4}$-alkylene groups specified above are intended to include those alkyl or alkylene groups of the designated length in either a linear or branched or cyclic configuration as permitted. Examples of linear alkyl are methyl, ethyl, propyl, butyl, pentyl, and hexyl and their corresponding divalent moieties, such as ethylene. Examples of branched alkyl are isopropyl, sec-butyl, tert-butyl, isopentyl, and isohexyl and their corresponding divalent moieties, such as isopropylene. Examples of cyclic alkyl are $C_{3-6}$-cycloalkyl such as cyclopropyl, cyclobutyl, cyclopentyl and cyclohexyl and their corresponding divalent moieties, such as cyclopropylene.

The $C_{1-6}$-alkoxy groups specified above are intended to include those alkoxy groups of the designated length in either a linear or branched or cyclic configuration. Examples of linear alkoxy are methoxy, ethoxy, propoxy, butoxy, pentoxy, and hexoxy. Examples of branched alkoxy are isopropoxy, sec-butoxy, tert-butoxy, isopentoxy, and isohexoxy. Examples of cyclic alkoxy are cyclopropyloxy, cyclobutyloxy, cyclopentyloxy and cyclohexyloxy.

The $C_{1-7}$-acyl groups specified above are intended to include those acyl groups of the designated length in either a linear or branched or cyclic configuration. Examples of linear acyl are formyl, acetyl, propionyl, butyryl, valeryl, etc. Examples of branched are isobutyryl, isovaleryl, pivaloyl, etc. Examples of cyclic are cyclopentylcarbonyl, cyclohexylcarbonyl, etc.

In the present context, the term "aryl" is intended to include monovalent carbocyclic aromatic ring moieties, being either monocyclic, bicyclic or polycyclic, e.g., phenyl and napthyl, optionally substituted with one or more $C_{1-6}$alkyl, $C_{1-6}$alkoxy, halogen, amino or aryl.

In the present context, the term "arylene" is intended to include divalent carbocyclic aromatic ring moieties, being either monocyclic, bicyclic or polycyclic, e.g. selected from the group consisting of phenylene and napthylene, optionally substituted with one or more $C_{1-6}$alkyl, $C_{1-6}$alkoxy, halogen, amino or aryl.

In the present context, the term "hetaryl" is intended to include monovalent heterocyclic aromatic ring moieties, being either monocyclic, bicyclic or polycyclic, e.g. selected from the group consisting of pyridyl, 1-H-tetrazol-5-yl, thiazolyl, imidazolyl, indolyl, pyrimidinyl, thiadiazolyl, pyrazolyl, oxazolyl, isoxazolyl, oxadiazolyl, thienyl, quinolinyl, pyrazinyl, or isothiazolyl, optionally substituted by one or more $C_{1-6}$alkyl, $C_{1-6}$alkoxy, halogen, amino or aryl.

In the present context, the term "hetarylene" is intended to include divalent heterocyclic aromatic ring moieties, being either monocyclic, bicyclic or polycyclic, e.g. selected from the group consisting of pyridinediyl, 1-H-tetrazolediyl, thiazoldiyl, imidazolediyl, indolediyl, pyrimidinediyl, thiadiazolediyl, pyrazolediyl, oxazolediyl, isoxazolediyl, oxadiazolediyl, thiophenediyl, quinolinediyl, pyrazinediyl, or isothiazolediyl, optionally substituted by one or more $C_{1-6}$alkyl, $C_{1-6}$alkoxy, halogen, amino or aryl.

In the present context, the term "heterocyclic system" is intended to include aromatic as well as non-aromatic ring moieties, which may be monocyclic, bicyclic or polycyclic, and contain in their ring structure at least one, such as one, two or three, nitrogen atom(s), and optionally one or more, such as one or two, other hetero atoms, e.g. sulphur or oxygen atoms. The heterocyclic system is preferably selected from pyrazole, pyridazine, triazine, indazole, phthalazine, cinnoline, pyrazolidine, pyrazoline, aziridine, dithiazine, pyrrol, imidazol, pyrazole, isoindole, indole, indazole, purine, pyrrolidine, pyrroline, imidazolidine, imidazoline, pyrazolidine, pyrazoline, piperidine, piperazine, indoline, isoindoline, or morpholine.

The term "halogen" is intended to include chlorine (Cl), fluorine (F), bromine (Br) and iodine (I).

Exemplification

The present invention will now be illustrated by the following Example, which are not intended to be limiting in any way.

Study in Rat Model

The experiment was conducted to determine the prokinetic effect of the growth hormone secretagogue RC-1139. The compound RCA139 was tested in normal conscious animals, as well as in the post-operative period, including concomitant morphine administration, to mimic the clinical condition where most post-operative patients are receiving opiate analgesia that can contribute to or increase post-operative gastrointestinal ileus.

Study Design

Normal Conscious Rats

Gastric emptying in healthy rats was studied. A total of eighteen (n=18) animals were administered RC-1139 (six animals (n=6)/group). Animals were administered a distilled water solution (1.5 ml) containing 1.5% methylcellulose and technitium-99m ($^{99m}$Tc) (approximately 100,000 counts per minute) administered intragastrically through stainless steel tube in conscious rats. Ten (n=10) control animals were administered the methylcellulose solution but saline instead of RC-1139. The substances tested (saline vs. RC-1139) were injected intravenously at the end of the methylcellulose administration at time 0. The dose levels of RC-1139 were as follows: 0.25, 1.0 and 2.5 mg/kg. RC-1139 was given as a 1 min bolus and was well tolerated at all doses.

Gastric emptying was measured by the following technique. Animals were sacrificed by $CO_2$ inhalation and after 15 min and the abdomen was opened. Stomachs were clamped at the pylorus and cardia were removed and placed in test tubes for counting with the use of a gamma counter the amount of radioactivity left in the stomach. The results are shown in FIG. 1.

Post-Operative Ileus

Post-operative ileus was studied in nine (n=9) animals/group. Gastric ileus was induced as follows: the rats were anesthetized with isoflurane and submitted to laparotomy. The cecum was exteriorized and gently manipulated (patted between hands for 1 minute in saline-soaked gauze). Abdominal muscles were then closed with silk sutures and the animals were allowed to recover for 5 minutes before gavage for gastric emptying studies. A distilled water solution (1.5 ml) containing 1.5% methylcellulose and technitium-99m ($^{99m}$Tc) (approximately 100,000 counts per minute) was then administered intragastrically through stainless steel tube in conscious rats. The substances tested (saline vs. RC-1139) were injected intravenously at the end of the methylcellulose administration at time 0. The dose levels of RC-1139 were as follows: 1.0, 2.5 and 10 mg/kg. RC-1139 was given as a 1 min bolus and was well tolerated at all doses.

Figure 2:
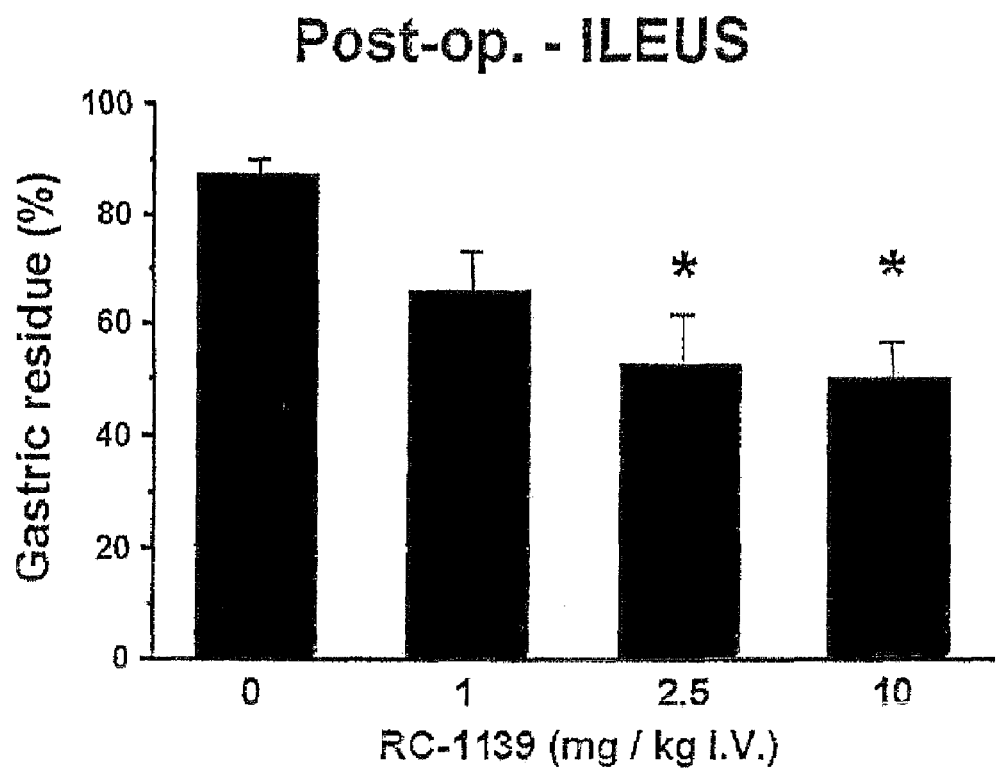
FIG. 2 is a bar graph of percentage of gastric emptying for rats with induced post-operative gastric ileus administered saline or RC-1139 at a dose of 1.0 mg/kg, 2.5 mg/kg or 10 mg/kg. The results demonstrate a statistically significant decrease in gastric residue at the 2.5 mg/kg dose and the 10 mg/kg dose.

Gastric emptying was measured by the following technique. Animals were sacrificed by $CO_2$ inhalation after 15 min and the abdomen was opened. Stomachs were clamped at the pylorus and cardia were removed and placed in test tubes for counting with the use of a gamma counter the amount of radioactivity left in the stomach. The results are shown in FIG. 2.

Post-Operative Ileus and Morphine

To study opiate analgesia induced post-operative ileus, eight (n=8) rats/group were administered morphine (4 mg/kg) thirty minutes (30 min) before methycellulose administration. As described above, gastric ileus was induced by submitting the rats to laparotomy after anesthesia with isoflurane. The cecum was exteriorized and gently manipulated (patted between hands for 1 minute in saline-soaked gauze). Abdominal muscles were then closed with silk sutures and the animals were allowed to recover for 5 minutes before gavage for gastric emptying studies. A distilled water solution (1.5 ml) containing 1.5% methylcellulose and technitium-99m ($^{99m}$Tc) (approximately 100,000 counts per minute) was then administered intragastrically through stainless steel tube in conscious rats. The substances tested (saline vs. RC-1139) were injected intravenously at the end of the methylcellulose administration at time 0. The dose levels were as follows: 2.5, 10 and 50 mg/kg. RC-1139 was given as a 1 min bolus and was well tolerated at all doses.

Figure 3:
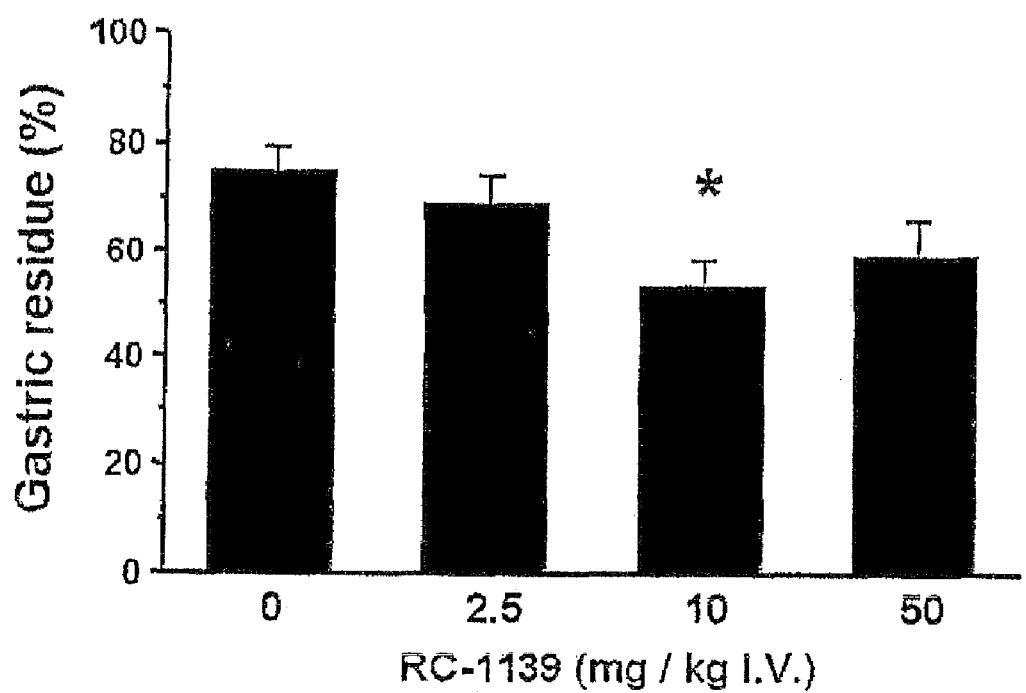
FIG. 3 is a bar graph of percentage of gastric emptying for rats with induced post-operative gastric ileus and morphine treatment (4 mg/kg), administered saline or RC-1139 at a dose of 2.5 mg/kg, 10 mg/kg or 50 mg/kg. The results demonstrate a statistically significant decrease in gastric residue at the 10 mg/kg dose of RC-1139.

Gastric emptying was measured by the following technique. Animals were killed by $CO_2$ inhalation after 15 min and the abdomen was opened. Stomachs were clamped at the pylorus and cardia were removed and placed in test tubes for counting with the use of a gamma counter the amount of radioactivity left in the stomach. The results are shown in FIG. 3.

Figure 4:
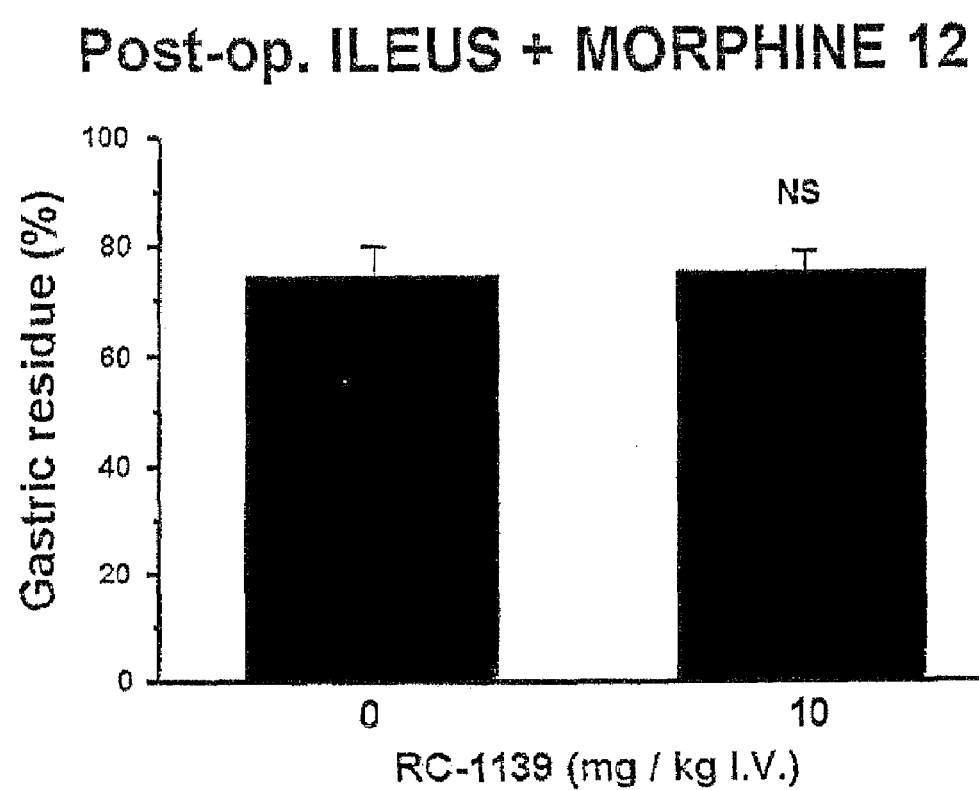
FIG. 4 is a bar graph of percentage of gastric emptying for rats with induced post-operative gastric ileus and morphine treatment (12 mg/kg), administered saline or RC-1139 at a dose of 10 mg/kg. The results show that at a 10 mg/kg dose, RC-1139 did not accelerate the delayed gastric emptying over the saline treated controls.

In order to study a situation in which an opiate would be overdosed, an experiment was conducted in rats with induced post-operative ileus as discussed above, however, the dose of morphine was 12 mg/kg. The results are shown in FIG. 4.

Figure 5:
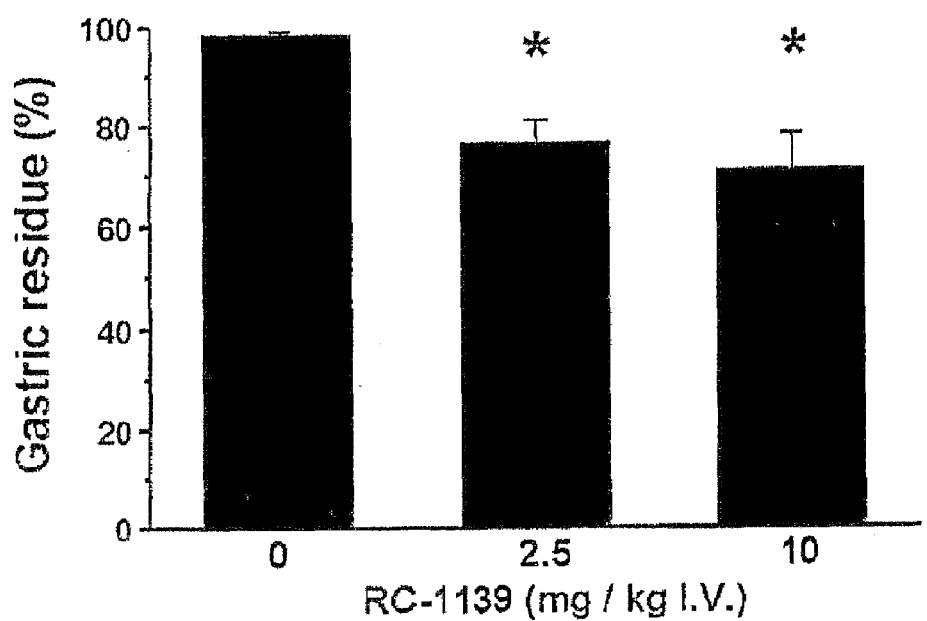
FIG. 5 is a bar graph of percentage of gastric emptying for normal rats with morphine treatment (4 mg/kg) administered saline or RC-1139 at a dose of 2.5 mg/kg or 10 mg/kg. The results demonstrate a statistically significant decrease in gastric residue at the 2.5 mg/kg dose and the 10 mg/kg dose of RC-1139.
Figure 6:
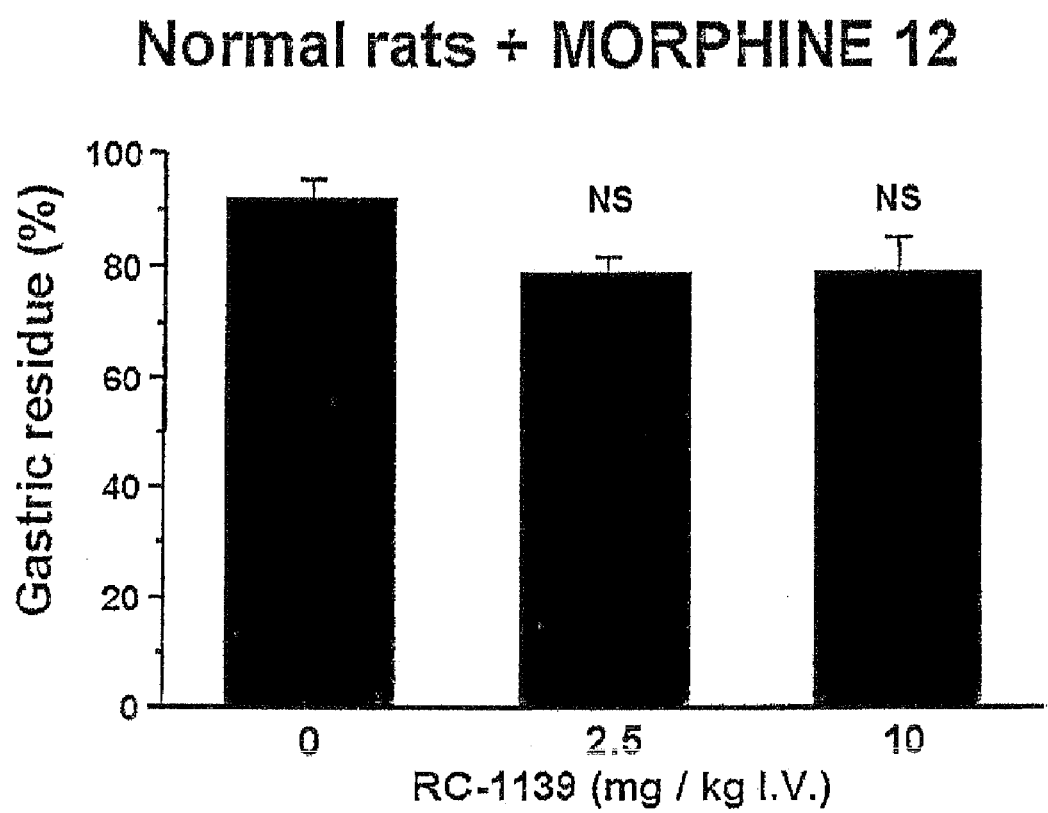
FIG. 6 is a bar graph of percentage of gastric emptying for normal rats with morphine treatment (12 mg/kg) administered saline or RC-1139 at a dose of 2.5 mg/kg or 10 mg/kg. The results show a decrease (non-statistically significant) in gastric residue at the 2.5 mg/kg dose and the 10 mg/kg dose of RC-1139.
Figure 7:
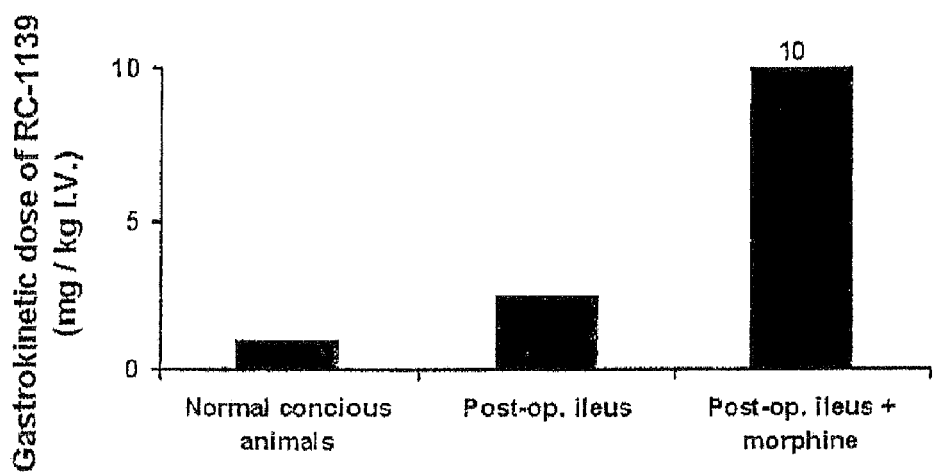
FIG. 7 is a bar graph of estimated effective doses of RC-1139 to stimulate gastric emptying in rats subjected to the experimental conditions described herein.

An experiment was also conducted in normal conscious rats as discussed above at both 4 mg/kg of morphine (FIG. 5) and 12 mg/kg of morphine (FIG. 6).

Study Endpoints

To assess gastric emptying, gastric residue remaining in the stomach was measured 15 min postingestion of the methycellulose solution by counting the amount of $^{99m}$Tc in the removed organ. Data expressed in percentage of the administered dose are shown as means±SEM. Statistical analysis was done by ANOVA (with Tukey-Kramer post-tests with one-to-one comparisons).

Results

Normal Conscious Rats

After 15 min, 47.1±6.6% of the administered methylcellulose was left in the stomach (n=10). In animals (n=6) treated with RC-1139, at doses of 0.25, 1, 2.5 mg/kg, the amount of the methylcellulose left in the stomach was decreased respectively to 36±8.6 (p=NS), 11.9±3.6 (p<0.01) and 10.5±3.8 (p<0.01).

Post-Operative Ileus

In saline treated animals, gastric emptying was delayed since 88±2.5% of the administered methylcellulose was left in the stomach after 15 min. Animals (n=9) treated with RC-1139 at a dose of 1 mg/kg I.V. had a small non-significant decrease in their gastric residue (66.3±7.4%); when RC-1139 was given at a dose of 2.5 or 10 mg/kg I.V., gastric emptying was accelerated and restored to normal values (52.9±9.2 and 50.7±6.2% of gastric residue respectively; p<0.01).

Post-Operative Ileus and Morphine

Gastric emptying was slow in saline treated animals (n=8) (75.4±4.5% of residue) and this effect was not reversed by RC-1139 given at 2.5 mg/kg (69.4±5.3%), a dose that, as shown above, has been found effective to reverse post-operative ileus in absence of morphine. A higher dose of RC-1139

(10 mg/kg) was required to reverse opiate analgesia induced post-operative gastrointestinal ileus to normal emptying values (53.8±4.8%; $p<0.05$). A larger dose of 50 mg/kg provided no further improvement (59.5±8.5%).

In the experiment where an opiate overdose was mimicked in rats with induced post-operative ileus and 12 mg/kg of morphine, RC-1139 given at 10 mg/kg I.V. was unable to accelerate the delayed gastric emptying found in saline treated animals (75.7±3.3 vs. 75.1±4.9%; p=NS; n=6 animals/group).

In the experiment in normal conscious rats administered 4 mg/kg of morphine and 12 mg/kg of morphine, morphine was a strong inhibitor of gastric emptying in these animals (n=6/group). With the high dose of morphine (12 mg/kg), RC-1139 given at 2.5 or 10 mg/kg failed to accelerate the delayed gastric emptying (92.6±3.2 vs. 79.5±2.4 or 79.7±5.9%; p=NS). With the lower dose of morphine (4 mg/kg), the gastric residue (99.1±0.5%) could be decreased to 77±4.1 or 71.3±6.7% by RC-1139 at a dose of 2.5 mg/kg or 10 mg/kg respectively ($p<0.01$ for both); these values however were still higher than the normal gastric emptying found in normal basal conditions.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of stimulating colonic motility and treating post-operative ileus of the colon in a patient in need thereof, comprising administering to said patient a therapeutically effective amount of ipamorelin or a pharmaceutically acceptable salt, thereof, wherein said post-operative ileus is induced via opioid use.

2. The method of claim 1 wherein said post-operative ileus is induced via opioid use and gastrointestinal surgery.

3. The method of claim 1 comprising injection administration.

4. The method of claim 1, wherein said treatment consists essentially of said administration.

5. The method of claim 1 comprising administration of from 0.01-2,600 mg of ipamorelin per day.

6. A method of simultaneously treating post-operative ileus of the colon and opioid-induced gastric stasis in a patient in need thereof, comprising administering to said patient a therapeutically effective amount of ipamorelin or a pharmaceutically acceptable salt, thereof.

7. The method of claim 6 comprising injection administration.

8. The method of claim 6 wherein said treatment consists essentially of said administration.

9. The method of claim 6 comprising administration of from 0.01-2,600 mg of ipamorelin per day.

10. The method of claim 6 wherein said patient is recovering from abdomen surgery.

11. A method of treating post-operative ileus in a patient in need thereof, comprising administering to said patient a therapeutically effective amount of ipamorelin or a pharmaceutically acceptable salt thereof, wherein said post-operative ileus is induced via opioid use.

12. The method of claim 11 wherein said post-operative ileus is induced via opioid use and gastrointestinal surgery.

13. The method of claim 11 comprising injection administration.

14. The method of claim 11 wherein said treatment consists essentially of said administration.

15. The method of claim 11 comprising administration of from 0.01-2,600 mg of ipamorelin per day.

16. The method of claim 11 wherein said patient is recovering from abdomen surgery.

* * * * *